US011067583B2

(12) United States Patent
Sajadi et al.

(10) Patent No.: US 11,067,583 B2
(45) Date of Patent: Jul. 20, 2021

(54) METHODS OF MAKING ACTIVE ANTIBODIES FROM BIOLOGICAL FLUIDS

(71) Applicants: University of Maryland, Baltimore, Baltimore, MD (US); The United States of America as represented by the Department of Veterans Affairs, Washington, DC (US)

(72) Inventors: Mohammad Sajadi, Cockeysville, MD (US); Anthony DeVico, Alexandria, VA (US); George Lewis, Baltimore, MD (US)

(73) Assignees: UNIVERSITY OF MARYLAND, BALTIMORE, Baltimore, MD (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/302,525

(22) PCT Filed: May 25, 2017

(86) PCT No.: PCT/US2017/034581
§ 371 (c)(1),
(2) Date: Nov. 16, 2018

(87) PCT Pub. No.: WO2017/205694
PCT Pub. Date: Nov. 30, 2017

(65) Prior Publication Data
US 2020/0182883 A1 Jun. 11, 2020

Related U.S. Application Data

(60) Provisional application No. 62/341,211, filed on May 25, 2016.

(51) Int. Cl.
| | |
|---|---|
| *C07K 16/00* | (2006.01) |
| *C07H 21/04* | (2006.01) |
| *C12P 21/08* | (2006.01) |
| *A61K 39/395* | (2006.01) |
| *C07K 1/00* | (2006.01) |
| *G01N 33/68* | (2006.01) |
| *C07K 1/22* | (2006.01) |
| *C07K 16/10* | (2006.01) |
| *H01J 49/26* | (2006.01) |

(52) U.S. Cl.
CPC .......... *G01N 33/6854* (2013.01); *C07K 1/22* (2013.01); *C07K 16/1054* (2013.01); *C07K 16/1063* (2013.01); *C07K 16/1072* (2013.01); *C07K 2317/565* (2013.01); *C07K 2317/76* (2013.01); *H01J 49/26* (2013.01)

(58) Field of Classification Search
CPC .......... A61P 25/00; A61P 25/28; A61P 29/00; A61P 31/04; A61P 35/00
See application file for complete search history.

(56) References Cited

U.S. PATENT DOCUMENTS

| 5,237,053 A | 8/1993 | Dorner |
| 9,115,399 B2 | 8/2015 | Panigrahi |
| 9,146,241 B2 | 9/2015 | Lavinder |
| 2011/0223615 A1* | 9/2011 | Lewis .............. G01N 33/56988 435/7.1 |
| 2016/0034639 A1* | 2/2016 | Reddy .................... G16B 40/00 702/20 |

FOREIGN PATENT DOCUMENTS

| WO | 2005030123 A2 | 4/2005 |
| WO | 2005077106 A3 | 8/2005 |

(Continued)

OTHER PUBLICATIONS

European Extended Search Report from Appl. No. EP17803634, dated Dec. 18, 2019.
Sato et al., Proteomics-directed cloning of circulating antiviral human monoclanal antibodies, Nature Biotechnology, vol. 30, (2012), p. 1039-1043.
Wine et al., Molecular deconvolution of the monoclonal antibodies that comprise the polyclonal serum response, Proceedings of the National Academy of Sciences, vol. 110 (2013), p. 2993-2998.
Cheung et al., A proteomics approach for the identification and cloning of monoclonal antibodies form serum, Nature Biotechnology, (2012), p. 1087-0156.

(Continued)

*Primary Examiner* — Barry A Chestnut
(74) *Attorney, Agent, or Firm* — Nevrivy Patent Law Group P.L.L.C.

(57) ABSTRACT

The present invention provides a method of making an antibody by identifying a circulating antibody with activity from a subject comprising i) subjecting biological fluid selected from the group consisting of blood, plasma and serum and combinations thereof from the subject to one or more rounds of affinity chromatography to purify the circulating antibody; ii) optionally further subjecting the circulating antibody to isoelectric focusing to purify the circulating antibody based on charge; iii) testing the purified circulating antibody for activity; iv) digesting the purified circulating antibody from parts i) or ii) to create an antibody fragment; v) subjecting the antibody fragment to mass spectrometry to generate a mass assignment and a deduced amino acid sequence of the antibody fragment; vi) comparing the deduced amino acid sequence with an amino acid sequence of an antibody generated from the subject's B-cells to identify an antibody sequence that matches the deduced amino acid sequence; vii) generating an antibody comprising light chain and heavy chain CDR sequences of the B-cell antibody that matches the deducted amino acid sequence of party vi); and viii) testing the antibody of part vii) for activity.

30 Claims, 24 Drawing Sheets
Specification includes a Sequence Listing.

(56) References Cited

FOREIGN PATENT DOCUMENTS

| WO | 2009046984 A1 | 4/2009 |
| WO | 2013078455 A2 | 5/2013 |
| WO | 2013185180 A1 | 12/2013 |

OTHER PUBLICATIONS

Wang et al., Antigen identification and characterization of lung cancer specific monoclonal antibodies produced by mAb proteomics, Journal of Proteome Research, American Chemical Society, vol. 9, (2010), p. 1834-1842.

Sajadi et al., Signature Biochemical Properties of Broadly Cross-Reactive HIV-1 Neutralizing Antibodies in Human Plasma, Journal of Virology, vol. 86, (2012), p. 5014-5025.

International Search Report from Appl. No. PCT/US2017034581, dated Aug. 14, 2017.

* cited by examiner

A.

B.

| Virus ID | N60 gp120-Ig IC50 | N60-P23 IC50 |
|---|---|---|
| HIV-001428-2.42 | | |
| 6535.3 | | |
| AC10.0.29 | | |
| RHPA4259.7 | | |
| Q23.17 | | |
| Q259.d2.17 | | |
| 3365.v2.c2 | | |
| CAAN5342.A2 | | |
| ZM53M.PB12 | | |
| 900456_A3_4 | | |
| REJO4541.67 | | |
| CNE18 | | |
| 0842.d12 | | |
| Ce1086_B2 | | |
| 1006_11_C3_1601 | | |
| 9301.v1.c24 | | |
| 6041.v3.c23 | | |
| Q769.d22 | | |
| 1012_11_TC21_3257 | | |
| TRO.11 | | |
| 0815.v3.c3 | | |
| SC422661.8 | | |
| Du156.12 | | |
| T250-4 | | |
| C3347.c11 | | |
| 191084 B7-19 | | |
| 7030102001E5(Rev-) | | |
| Du422.1 | | |
| ZM197M.PB7 | | |
| R2184.c04 | | |
| PVO.4 | | |
| 6535_MC11_2344 | | |
| CNE8 | | |
| ZM-4 | | |
| WEAU_d15_410_787 | | |
| THRO4156.18 | | |
| 62357_14_D3_4589 | | |
| TRJO4551.58 | | |
| X1254_c3 | | |
| A07412M1.vrc12 | | |

| Virus ID | N60 gp120-lg IC50 | N60-P23 IC50 |
|---|---|---|
| BF1266_431a | | |
| 3103.v3.c10 | | |
| 1058_10_TA11_1826 | | |
| WITO4160.33 | | |
| 1394C9G1(Rev-) | | |
| Ce703010054_2A2 | | |
| CNE8 | | |
| 191955_A11 | | |
| X2088_c9 | | |
| CNE21 | | |
| 191821_E6_1 | | |
| 1054_07_TC4_1499 | | |
| BJOX015000.11.5 | | |
| R1166.c01 | | |
| T257-31 | | |
| 6240_08_TA5_4622 | | |
| CNE17 | | |
| CNE30 | | |
| ZM214M.PL15 | | |
| ZM109F.PB4 | | |
| BJOX009000.02.4 | | |
| ZM247v1(Rev-) | | |
| M6208.A1 | | |
| T251-18 | | |
| 246F C1G | | |
| Q461.e2 | | |
| 231965.c02 | | |
| HIV-16845-2.22 | | |
| Ce2060_G9 | | |
| Du172.17 | | |
| CAP45.2.00.G3 | | |
| Ce1172_H1 | | |
| 928-28 | | |
| T278-50 | | |
| 211-9 | | |
| 620345.c01 | | |
| C1080.c03 | | |
| R2356.c06 | | |
| BJOX010000.06.2 | | |
| 3016.v5.c45 | | |
| 89-F1_2_25 | | |

FIG. 9

| FFE Fraction | 29 | 33 | 39 | 40 | 46 | 57 | 60 | 61 |
|---|---|---|---|---|---|---|---|---|
| pI | 6.93 | 7.3 | 7.61 | 7.73 | 8.39 | 8.65 | 8.86 | 8.89 |
| ELISA | | | | | | | | |
| gp120 | - | + | - | - | + | + | + | + |
| D368R | + | + | - | - | + | - | - | - |
| FLSC | +++ | +++ | ++ | ++ | + | + | + | + |
| Core | - | - | - | - | + | + | ++ | ++ |
| | | | | | | | | |
| Neutralization | - | - | - | - | - | + | + | + |

| mAb | N60P48 | N60P39 | N60P36 | N60P47 | N60P30 | N60P2.1 | N60P22 | N60P23 | N60P25.1 N60P31.1 |
|---|---|---|---|---|---|---|---|---|---|
| pI | 7.2 | 7.22 | 7.57 | 7.8 | 8.4 | 8.67 | 8.84 | 8.86 | 8.94 |
| ELISA | | | | | | | | | |
| gp120 | - | + | - | - | + | +++ | +++ | ++++ | - |
| D368R | - | + | - | - | + | - | - | - | - |
| FLSC | +++ | +++ | +++ | +++ | +++ | - | + | - | - |
| Core | - | - | - | - | - | - | ++++ | - | - |
| | | | | | | | | | |
| Neutralization | - | - | - | - | - | + | - | + | + |

SEQUENCE LISTING

<160> NUMBER OF SEQ ID NOS: 53

<210> SEQ ID NO 1
<211> LENGTH: 120
<212> TYPE: PRT
<213> ORGANISM: Homo sapiens

<400> SEQUENCE: 1

His Val Gln Leu Val Gln Ser Gly Thr Glu Val Lys Arg Pro Gly Ala
1               5                   10                  15

Ser Val Arg Ile Ser Cys Ala Ser Ser Gly Tyr Thr Phe Ser Asn Tyr
            20                  25                  30

Phe Ile His Trp Val Arg Gln Ala Pro Gly Arg Gly Leu Glu Trp Met
        35                  40                  45

Gly Trp Met Asn Pro Leu Arg Gly Ala Val Asn Tyr Ser Gly Lys Phe
    50                  55                  60

Gln Gly Arg Val Thr Met Thr Arg Asp Ile Tyr Thr Glu Thr Ser Phe
65                  70                  75                  80

Met Val Leu Ser Gly Leu Arg Ser Asp Asp Thr Ala Ile Tyr Phe Cys
                85                  90                  95

Ala Arg Gly Arg Asp Gly Tyr Glu Tyr Gly Phe Asn Pro Trp Gly Gln
            100                 105                 110

Gly Thr Leu Val Thr Val Ser Ser
        115                 120

<210> SEQ ID NO 2
<211> LENGTH: 8
<212> TYPE: PRT
<213> ORGANISM: Homo sapiens

<400> SEQUENCE: 2

Gly Tyr Thr Phe Ser Asn Tyr Phe
1               5

<210> SEQ ID NO 3
<211> LENGTH: 8
<212> TYPE: PRT
<213> ORGANISM: Homo sapiens

<400> SEQUENCE: 3

Met Asn Pro Leu Arg Gly Ala Val
1               5

<210> SEQ ID NO 4
<211> LENGTH: 13
<212> TYPE: PRT
<213> ORGANISM: Homo sapiens

<400> SEQUENCE: 4

Ala Arg Gly Arg Asp Gly Tyr Glu Tyr Gly Phe Asn Pro
1               5                   10

<210> SEQ ID NO 5
<211> LENGTH: 360
<212> TYPE: DNA
<213> ORGANISM: Homo sapiens

<400> SEQUENCE: 5
catgtgcagc tggtgcagtc tgggactgag gtgaagaggc ctggggcctc agtgaggatc      60
tcctgcgcgt cttctggata caccttcagc aactacttta ttcactgggt gcgacaggcc     120

```
cctggacgag ggcttgagtg gatgggatgg atgaacccte teagaggtge cgtaaactat    180 tcagggaagt ttcagggcag ggtcaccatg accaggaca tctacaccga aacatccttc    240
atggtgctga gcgggctgag atctgacgac acggccatct atttctgtgc gagaggtaga    300
gatggttatg agtacgggtt caaccccetgg ggccagggaa ccctggtcac cgtctcctca    360
```

<210> SEQ ID NO 6
<211> LENGTH: 101
<212> TYPE: PRT
<213> ORGANISM: Homo sapiens

<400> SEQUENCE: 6

Cys Tyr Val Gln Thr Gln Ser Pro Ser Thr Leu Tyr Ala Ser Val Gly
1               5                   10                  15

Asp Arg Val Thr Ile Thr Cys Arg Ser Ser Gln Ser Gly Trp Lys Ala
            20                  25                  30

Trp Tyr Gln Gln Lys Pro Gly Lys Ala Pro Lys Leu Leu Ile Tyr Lys
        35                  40                  45

Ser Ser Thr Leu Glu Ser Gly Val Pro Ser Arg Phe Ser Gly Ser Asp
    50                  55                  60

Ser Gly Thr Glu Phe Asn Leu Thr Ile Thr Ser Leu Gln Pro Asp Asp
65                  70                  75                  80

Phe Ala Thr Tyr Phe Cys Gln His Phe Glu Thr Phe Gly Gln Gly Thr
                85                  90                  95

Arg Val Glu Val Arg
            100

<210> SEQ ID NO 7
<211> LENGTH: 4
<212> TYPE: PRT
<213> ORGANISM: Homo sapiens

<400> SEQUENCE: 7

Gln Ser Gly Trp
1

<210> SEQ ID NO 8
<211> LENGTH: 5
<212> TYPE: PRT
<213> ORGANISM: Homo sapiens

<400> SEQUENCE: 8

Gln His Phe Glu Thr
1               5

<210> SEQ ID NO 9
<211> LENGTH: 303
<212> TYPE: DNA
<213> ORGANISM: Homo sapiens

<400> SEQUENCE: 9

```
tgcttcgtgc agtcccagtc tccttccacc ctgtatgcat ctgtaggaga caaaatcacc    60
atcacttgcc ggtccagtca gagtggttgg aaggcctggt atcagcagaa accagggaaa    120
gcccctaagc tcctgatcta taaatcctcc attttggaaa ctggggtccc atcaaggttc    180
atcggcagtg attctgggac agaattcact ctcaccatca gcagcctgca gcctgatgat    240
tttgcaactt attactgcca acattttgag acgttcggcc aagggaccag ggtgcaagtc    300
aga                                                                  303
```

<210> SEQ ID NO 10
<211> LENGTH: 120
<212> TYPE: PRT
<213> ORGANISM: Homo sapiens

<400> SEQUENCE: 10

Arg Ala Gln Leu Val Gln Ser Gly Pro Glu Val Lys Lys Pro Gly Ala
1               5                   10                  15

Ser Val Arg Ile Ser Cys Ala Ala Ser Gly Tyr Thr Phe Val Asp Ser
            20                  25                  30

Phe Ile His Trp Leu Arg Gln Ala Pro Gly Gln Gly Leu Glu Trp Ile
        35                  40                  45

Gly Trp Ile Asn Pro Leu Arg Gly Gly Val Asn Tyr Ser Gly Arg Phe
    50                  55                  60

Gln Gly Arg Val Ala Met Thr Arg Asn Thr Phe Thr Glu Thr Val Tyr
65                  70                  75                  80

Met Asp Ile Asn Gly Leu Thr Pro Asp Thr Ala Thr Tyr Phe Cys
                85                  90                  95

Val Arg Ala Pro Asp Ser Tyr Asp Arg Gly Tyr Asp Ala Trp Gly Gln
            100                 105                 110

Gly Thr Arg Val Ile Val Thr Ser
        115                 120

<210> SEQ ID NO 11
<211> LENGTH: 8
<212> TYPE: PRT
<213> ORGANISM: Homo sapiens

<400> SEQUENCE: 11

Gly Tyr Thr Phe Val Asp Ser Phe
1               5

<210> SEQ ID NO 12
<211> LENGTH: 8
<212> TYPE: PRT
<213> ORGANISM: Homo sapiens

<400> SEQUENCE: 12

Ile Asn Pro Leu Arg Gly Gly Val
1               5

<210> SEQ ID NO 13
<211> LENGTH: 13
<212> TYPE: PRT
<213> ORGANISM: Homo sapiens

<400> SEQUENCE: 13

Val Arg Ala Pro Asp Ser Tyr Asp Arg Gly Tyr Asp Ala
1               5                   10

<210> SEQ ID NO 14
<211> LENGTH: 360
<212> TYPE: DNA
<213> ORGANISM: Homo sapiens

<400> SEQUENCE: 14
cgggcgcagc tggtgcagtc tgggcctgag gtgaagaagc ctggggcctc agtgaggatc    60
tcctgcgcgg cttctggata caccttcgtc gattcctttca tccactggct gcgacaggcc   120
cctggacaag ggcttgagtg gataggatgg atcaaccctc tccgtggtgg cgtaaactat   180

```
tcaggcaggt tcagggcag ggtcgccatg accaggaaca cgttcaccga gacagtctac      240
atggacatca acgggctgac acctgacgac acggccacgt atttctgtgt gagagccccc      300
gattcgtacg acagagggta cgacgcctgg ggccaaggaa cccgggtcat cgtcacctca      360
```

<210> SEQ ID NO 15
<211> LENGTH: 100
<212> TYPE: PRT
<213> ORGANISM: Homo sapiens

<400> SEQUENCE: 15

Tyr Ile Gln Val Thr Gln Ser Pro Ser Thr Leu Ser Ala Ser Ile Gly
1               5                   10                  15

Asp Thr Val Thr Ile Thr Cys Arg Ala Ser Glu Gly Trp Leu Ala Trp
            20                  25                  30

Tyr Gln Gln Lys Pro Gly Lys Ala Pro Lys Leu Ile Ile Tyr Lys Thr
        35                  40                  45

Ser Thr Leu Glu Arg Gly Val Pro Ser Arg Phe Ser Gly Ser Val Ser
    50                  55                  60

Gly Ala Asp Phe Thr Leu Thr Ile Ser Gly Leu Gln Ser Asp Asp Phe
65                  70                  75                  80

Ala Thr Tyr Tyr Cys Gln Lys Phe Glu Phe Phe Gly Gln Gly Thr Val
                85                  90                  95

Val Asp Met Lys
            100

<210> SEQ ID NO 16
<211> LENGTH: 5
<212> TYPE: PRT
<213> ORGANISM: Homo sapiens

<400> SEQUENCE: 16

Gln Lys Phe Glu Phe
1               5

<210> SEQ ID NO 17
<211> LENGTH: 300
<212> TYPE: DNA
<213> ORGANISM: Homo sapiens

<400> SEQUENCE: 17

```
tacatccagg tgacccagtc tccttccacc ctgtctgcat ctataggaga cacagtcacc      60
atcacttgcc gggccagtga gggttggttg gcctggtatc agcagaaacc agggaaagcc     120
cctaagctca taatttataa gacctccact ttggaaagag gggtcccatc aaggttcagc     180
ggcagtgtat ctggggcaga cttcactctc accatcagcg gcctgcagtc tgatgatttt     240
gcaacttatt actgccaaaa gtttgaattt tttggccagg gaccgtggt ggacatgaaa     300
```

<210> SEQ ID NO 18
<211> LENGTH: 120
<212> TYPE: PRT
<213> ORGANISM: Homo sapiens

<400> SEQUENCE: 18

Gln Ile Glu Leu Val Gln Ser Gly Thr Glu Val Lys Arg Pro Gly Ala
1               5                   10                  15

Ser Val Arg Ile Ser Cys Ala Ser Ser Gly Tyr Arg Phe Thr Asn Tyr
            20                  25                  30

Phe Ile His Trp Val Arg Gln Ala Pro Gly Arg Gly Leu Glu Trp Met

```
            35                  40                  45
Gly Trp Met Asn Pro Leu His Gly Gly Val Asn Tyr Ser Gly Arg Phe
        50                  55                  60
Gln Gly Arg Val Thr Met Thr Arg Asp Ile Tyr Thr Glu Thr Ser Phe
65                  70                  75                  80
Met Val Leu Ser Gly Leu Thr Ser Asp Asp Thr Ala Ile Tyr Phe Cys
                85                  90                  95
Thr Arg Gly Arg Asp Gly Tyr Asp Asp Gly Phe His Pro Trp Gly Gln
            100                 105                 110
Gly Thr Leu Val Thr Val Ser Ala
        115                 120

<210> SEQ ID NO 19
<211> LENGTH: 8
<212> TYPE: PRT
<213> ORGANISM: Homo sapiens

<400> SEQUENCE: 19

Gly Tyr Arg Phe Thr Asn Tyr Phe
1               5

<210> SEQ ID NO 20
<211> LENGTH: 8
<212> TYPE: PRT
<213> ORGANISM: Homo sapiens

<400> SEQUENCE: 20

Met Asn Pro Leu His Gly Gly Val
1               5

<210> SEQ ID NO 21
<211> LENGTH: 13
<212> TYPE: PRT
<213> ORGANISM: Homo sapiens

<400> SEQUENCE: 21

Thr Arg Gly Arg Asp Gly Tyr Asp Asp Gly Phe His Pro
1               5                   10

<210> SEQ ID NO 22
<211> LENGTH: 360
<212> TYPE: DNA
<213> ORGANISM: Homo sapiens

<400> SEQUENCE: 22
cagatcgagc tggtgcagtc tgggactgag gtgaagaggc ctggggcctc agtgaggatc      60
tcctgcgcgt cttctggata cagattcacc aactacttta tccactgggt gcgacaggcc    120
cctggacgag ggcttgagtg gatgggatgg atgaaccctc tccacggtgg cgtaaactat    180
tcagggaggt ttcagggcag ggtcaccatg accaggaca tctacaccga gacatccttc     240
atggtgctga gcgggctgac atctgacgac acggccatat atttctgtac gagaggcagg    300
gacggttatg acgacgggtt ccaccctgg ggccaaggaa ccctggtcac cgtctccgca     360

<210> SEQ ID NO 23
<211> LENGTH: 100
<212> TYPE: PRT
<213> ORGANISM: Homo sapiens

<400> SEQUENCE: 23

Tyr Val Gln Ser Gln Ser Pro Ser Thr Leu Tyr Ala Ser Val Gly Asp
```

-continued

```
              1               5                  10                 15
Lys Ile Thr Ile Thr Cys Arg Ser Ser Gln Ser Gly Trp Lys Ala Trp
             20                  25                 30

Tyr Gln Gln Lys Pro Gly Lys Ala Pro Lys Leu Leu Ile Tyr Lys Ser
         35                  40                 45

Ser Ile Leu Glu Thr Gly Val Pro Ser Arg Phe Ser Gly Ser Asp Ser
     50                  55                 60

Gly Thr Glu Phe Thr Leu Thr Ile Ser Ser Leu Gln Pro Asp Asp Phe
 65                  70                 75                  80

Ala Thr Tyr Tyr Cys Gln His Phe Glu Thr Phe Gly Gln Gly Thr Arg
                 85                  90                 95

Val Gln Val Arg
        100
```

<210> SEQ ID NO 24
<211> LENGTH: 4
<212> TYPE: PRT
<213> ORGANISM: Homo sapiens

<400> SEQUENCE: 24

Gln Ser Gly Trp
1

<210> SEQ ID NO 25
<211> LENGTH: 5
<212> TYPE: PRT
<213> ORGANISM: Homo sapiens

<400> SEQUENCE: 25

Gln His Phe Glu Thr
1               5

<210> SEQ ID NO 26
<211> LENGTH: 300
<212> TYPE: DNA
<213> ORGANISM: Homo sapiens

<400> SEQUENCE: 26
tacgtgcagt cccagtctcc ttccaccctg tatgcatctg taggagacaa aatcaccatc      60
acttgccggt ccagtcagag tggttggaag gcctggtatc agcagaaacc agggaaagcc     120
cctaagctcc tgatctataa atcctccatt ttggaaactg gggtcccatc aaggttcagc     180
ggcagtgatt ctgggacaga attcactctc accatcagca gcctgcagcc tgatgatttt     240
gcaacttatt actgccaaca ttttgagacg ttcggccaag ggaccagggt gcaagtcaga     300

<210> SEQ ID NO 27
<211> LENGTH: 119
<212> TYPE: PRT
<213> ORGANISM: Homo sapiens

<400> SEQUENCE: 27

```
              1               5                  10                 15
Gln Val Gln Leu Gln Glu Ser Gly Pro Gly Leu Val Lys Pro Ser Gln
             20                  25                 30

Thr Leu Ser Leu Thr Cys Thr Val Ser Gly Gly Ser Ile Asn Ser Gly
         35                  40                 45

Gly Tyr Phe Trp Thr Trp Ile Arg Gln Glu Pro Gly Lys Gly Leu Glu
     50                  55                 60

Trp Ile Gly His Val His Ser Ser Gly Thr Thr Ser Tyr Asn Pro Ser
```

```
Leu Lys Ser Arg Leu Thr Ile Ser Leu Asp Ser Ser Lys Asn Gln Phe
 65                  70                  75                  80

Ser Leu Asn Leu Thr Ser Val Thr Ala Ala Asp Thr Ala Val Tyr Tyr
                 85                  90                  95

Cys Ala Ser Gln Gly Arg Leu Gly Ile Gly Asp Tyr Trp Gly Gln Gly
            100                 105                 110

Ala Leu Val Val Val Ser Ser
        115

<210> SEQ ID NO 28
<211> LENGTH: 10
<212> TYPE: PRT
<213> ORGANISM: Homo sapiens

<400> SEQUENCE: 28

Gly Gly Ser Ile Asn Ser Gly Gly Tyr Phe
1               5                   10

<210> SEQ ID NO 29
<211> LENGTH: 9
<212> TYPE: PRT
<213> ORGANISM: Homo sapiens

<400> SEQUENCE: 29

Val His Ser Ser Gly Thr Thr Ser Tyr
1               5

<210> SEQ ID NO 30
<211> LENGTH: 11
<212> TYPE: PRT
<213> ORGANISM: Homo sapiens

<400> SEQUENCE: 30

Ala Ser Gln Gly Arg Leu Gly Ile Gly Asp Tyr
1               5                   10

<210> SEQ ID NO 31
<211> LENGTH: 357
<212> TYPE: DNA
<213> ORGANISM: Homo sapiens

<400> SEQUENCE: 31
caggtgcagc tgcaggagtc gggcccagga ctggtgaagc cttcacagac cctgtccctc      60
acttgcactg tctctggtgg ctccatcaac agtggtggtt acttctggac ctggatccgc     120
caggaaccag ggaagggcct ggagtggatt ggacacgtcc attccagtgg caccacctcc     180
tacaatccgt ccctcaagag ccgactcacc atatcgctag actcctctaa gaaccagttt     240
tccctaaacc tgacctcagt gactgccgcg gacacggccg tatattactg tgcgagtcaa     300
gggagactgg ggatcgggga ctactggggc caggagccc tggtcgtcgt ctcctca        357

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser His Leu
             20                  25                  30
```

Val Asn Trp Tyr Gln Gln Lys Pro Gly Lys Ala Pro Lys Pro Leu Ile
        35                  40                  45

Tyr Thr Val Ser Ser Leu His Ser Gly Val Pro Ser Arg Ile Ser Gly
    50                  55                  60

Ser Gly Ser Glu Thr Glu Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Arg
                85                  90                  95

Thr Phe Gly Gln Gly Thr Arg Val Asp Leu Lys
            100                 105

<210> SEQ ID NO 33
<211> LENGTH: 6
<212> TYPE: PRT
<213> ORGANISM: Homo sapiens

<400> SEQUENCE: 33

Gln Gly Val Ser His Leu
1               5

<210> SEQ ID NO 34
<211> LENGTH: 9
<212> TYPE: PRT
<213> ORGANISM: Homo sapiens

<400> SEQUENCE: 34

Gln Gln Thr Tyr Ser Ser Pro Arg Thr
1               5

<210> SEQ ID NO 35
<211> LENGTH: 321
<212> TYPE: DNA
<213> ORGANISM: Homo sapiens

<400> SEQUENCE: 35
gacatccaga tgacccagtc tccttcctcc ctgtctgcat ctgtgggaga cagagtcacc      60
atcacttgcc gggcaagtca gggcgttagt cacttggtaa attggtatca acagaagcca     120
gggaaagccc ctaagcccct gatctatact gtatccagtt tgcacagtgg ggtcccttca     180
aggatcagtg gcagtggatc tgagacagag ttcactctca ccatcagcag tctgcaacct     240
gaagatttcg caacttacta ctgtcaacag acttacagta gtcctcggac gttcggccaa     300
gggaccaggg tggatctcaa a                                               321

<210> SEQ ID NO 36
<211> LENGTH: 119
<212> TYPE: PRT
<213> ORGANISM: Homo sapiens

<400> SEQUENCE: 36

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Phe Trp Thr Trp Ile Arg Gln Glu Pro Gly Lys Gly Leu Glu
        35                  40                  45

Trp Ile Gly His Ile His Tyr Thr Gly Thr Thr Ser Tyr Asn Pro Ser
    50                  55                  60

Leu Lys Ser Arg Leu Thr Ile Ser Leu Asp Ser Ser Lys Asn Gln Phe

```
                65                  70                  75                  80
Ser Leu Asn Leu Thr Ser Val Thr Ala Ala Asp Thr Ala Val Tyr Tyr
                    85                  90                  95

Cys Ala Ser Gln Gly Arg Leu Gly Ser Gly Asp Tyr Trp Gly Gln Gly
                    100                 105                 110

Thr Leu Val Ile Val Ser Ser
        115

<210> SEQ ID NO 37
<211> LENGTH: 10
<212> TYPE: PRT
<213> ORGANISM: Homo sapiens

<400> SEQUENCE: 37

Gly Gly Ser Ile Ser Ser Gly Gly Tyr Phe
1               5                   10

<210> SEQ ID NO 38
<211> LENGTH: 9
<212> TYPE: PRT
<213> ORGANISM: Homo sapiens

<400> SEQUENCE: 38

Ile His Tyr Thr Gly Thr Thr Ser Tyr
1               5

<210> SEQ ID NO 39
<211> LENGTH: 11
<212> TYPE: PRT
<213> ORGANISM: Homo sapiens

<400> SEQUENCE: 39

Ala Ser Gln Gly Arg Leu Gly Ser Gly Asp Tyr
1               5                   10

<210> SEQ ID NO 40
<211> LENGTH: 357
<212> TYPE: DNA
<213> ORGANISM: Homo sapiens

<400> SEQUENCE: 40
caggtgcagc tgcaggagtc gggcccagga ctggtgaagc cttcacagac cctgtccctc       60
acttgcactg tctctggtgg ctccatcagc agtggtggtt acttctggac ctggatccgc      120
caggaaccag gcaagggcct ggagtggatt ggccacatcc attacactgg caccacctcc      180
tacaatccgt ccctcaagag ccgacttacc atatcacttg actcgtctaa gaaccagttt      240
tccctaaacc tgacctccgt gactgccgcg gacacggccg tttattactg tgcgagtcaa      300
gggagactgg ggagcgggga ctactggggc cagggaaccc tggtcatcgt ctcctca        357

<210> SEQ ID NO 41
<211> LENGTH: 107
<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser His Leu
            20                  25                  30

Val Asn Trp Tyr Gln Gln Lys Pro Gly Lys Ala Pro Lys Pro Leu Ile
```

```
                35                  40                  45
Tyr Ile Val Ser Ser Leu His Ser Gly Val Pro Ser Arg Phe Ser Gly
     50                  55                  60

Ser Gly Ser Glu Thr Asp Phe Thr Leu Thr Ile Ser Gly Leu Gln Pro
 65                  70                  75                  80

Glu Asp Phe Ala Thr Tyr Tyr Cys Gln Gln Thr Tyr Ser Ser Pro Arg
                 85                  90                  95

Thr Phe Gly Gln Gly Thr Arg Val Glu Leu Lys
            100                 105
```

<210> SEQ ID NO 42
<211> LENGTH: 6
<212> TYPE: PRT
<213> ORGANISM: Homo sapiens

<400> SEQUENCE: 42

```
Gln Ser Val Ser His Leu
1               5
```

<210> SEQ ID NO 43
<211> LENGTH: 9
<212> TYPE: PRT
<213> ORGANISM: Homo sapiens

<400> SEQUENCE: 43

```
Gln Gln Thr Tyr Ser Ser Pro Arg Thr
1               5
```

<210> SEQ ID NO 44
<211> LENGTH: 321
<212> TYPE: DNA
<213> ORGANISM: Homo sapiens

<400> SEQUENCE: 44

```
gacatccaga tgacccagtc tccatcctcc ctgtctgcat ctgtaggaga cagagtcacc    60
atcacttgcc gggcaagtca gagcgttagt cacttggtaa attggtatca acaaaagcca   120
gggaaagccc ctaagcccct gatttatatt gtatccagtt tacacagtgg ggtcccatca   180
aggttcagtg gcagtggatc tgagacggac ttcactctca ccatcagcgg tctgcaacct   240
gaagatttcg caacttacta ctgtcaacag acttacagta gtcctcggac gttcggccaa   300
gggaccaggg tggagctcaa a                                             321
```

<210> SEQ ID NO 45
<211> LENGTH: 117
<212> TYPE: PRT
<213> ORGANISM: Homo sapiens

<400> SEQUENCE: 45

```
Gln Val Gln Leu Arg Glu Ser Gly Pro Gly Leu Val Lys Pro Ser Ala
1               5                  10                  15

Thr Leu Ser Leu Thr Cys Ile Val Ser Gly Gly Ser Met Ser Gly Tyr
             20                  25                  30

Tyr Trp Ser Trp Ile Arg Gln Pro Pro Gly Lys Gly Leu Glu Trp Ile
         35                  40                  45

Gly His Ile Asp Asn Asn Glu Arg Thr Ile Ser Ser Pro Ser Leu Asn
     50                  55                  60

Ser Arg Val Thr Val Ser Pro Asp Thr Ser Arg Asn Arg Phe Thr Leu
 65                  70                  75                  80
```

```
Thr Leu Ser Ser Val Thr Ala Ala Asp Thr Ala Tyr Tyr Cys Ala
            85                  90                  95

Arg His Val Val Tyr Gly Gly Leu Asp Ile Trp Gly Gln Gly Thr Leu
        100                 105                 110

Val Thr Val Ser Ser
        115

<210> SEQ ID NO 46
<211> LENGTH: 8
<212> TYPE: PRT
<213> ORGANISM: Homo sapiens

<400> SEQUENCE: 46

Gly Gly Ser Met Ser Gly Tyr Tyr
1               5

<210> SEQ ID NO 47
<211> LENGTH: 9
<212> TYPE: PRT
<213> ORGANISM: Homo sapiens

<400> SEQUENCE: 47

Ile Asp Asn Asn Glu Arg Thr Ile Ser
1               5

<210> SEQ ID NO 48
<211> LENGTH: 11
<212> TYPE: PRT
<213> ORGANISM: Homo sapiens

<400> SEQUENCE: 48

Ala Arg His Val Val Tyr Gly Gly Leu Asp Ile
1               5                   10

<210> SEQ ID NO 49
<211> LENGTH: 351
<212> TYPE: DNA
<213> ORGANISM: Homo sapiens

<400> SEQUENCE: 49
caggtgcagc tgcgggagtc gggcccagga ctggtgaagc cttcggcgac cctctccctc      60
acgtgcattg tgtctggtgg ctccatgagt ggttattatt ggagttggat ccggcagccc     120
ccagggaagg gactggagtg gatcggacat attgataata atgagaggac catctccagc     180
ccctccctca acagtcgagt caccgtgtca ccagacacgt ccaggaatcg gttcaccctt     240
acactgagct ctgtgaccgc tgcagacacg gccacttatt actgtgcgag acacgtggtt     300 tacggggggac ttgatatctg gggccaaggg acactggtca ccgtctcttc a             351

<210> SEQ ID NO 50
<211> LENGTH: 107
<212> TYPE: PRT
<213> ORGANISM: Homo sapiens

<400> SEQUENCE: 50

Glu Ile Val Leu Thr Gln Ser Pro Gly Thr Leu Ser Leu Ser Pro Gly
1               5                   10                  15

Glu Arg Ala Ser Leu Ser Cys Arg Ala Ser Asp Ile Val Ser Ile Asn
            20                  25                  30

Tyr Phe Ala Trp Tyr Gln Gln Lys Pro Gly Gln Ala Pro Arg Leu Leu
        35                  40                  45
```

```
Ile Ser Gly Ala Ser Val Arg Ala Thr Gly Ile Pro Asp Arg Phe Ser
        50                  55                  60
Gly Ser Gly Ser Gly Thr Asp Phe Thr Leu Thr Ile Asn Arg Leu Glu
65                  70                  75                  80
Pro Glu Asp Val Ala Val Tyr Tyr Cys Gln Gln His Gly Ser Ser Pro
                85                  90                  95
Thr Phe Gly Gln Gly Thr Lys Val Glu Ile Lys
            100                 105

<210> SEQ ID NO 51
<211> LENGTH: 7
<212> TYPE: PRT
<213> ORGANISM: Homo sapiens

<400> SEQUENCE: 51

Asp Ile Val Ser Ile Asn Tyr
1               5

<210> SEQ ID NO 52
<211> LENGTH: 8
<212> TYPE: PRT
<213> ORGANISM: Homo sapiens

<400> SEQUENCE: 52

Gln Gln His Gly Ser Ser Pro Thr
1               5

<210> SEQ ID NO 53
<211> LENGTH: 321
<212> TYPE: DNA
<213> ORGANISM: Homo sapiens

<400> SEQUENCE: 53
gaaattgtgt tgacgcagtc tccgggcacc ctgtctttgt ctccagggga aagagcctcc      60
ctctcctgca gggccagtga cattgttagc atcaactact ttgcctggta ccagcagaaa     120
cctggccagg ctcccaggct cctcatctct ggtgcatccg tcagggccac tggcatccca     180
gacaggttca gtggcagtgg gtctgggaca gacttcactc tcaccatcaa cagactggag     240
cctgaagatg ttgcagtgta ttactgtcag caacatggta gctcaccgac gttcggccaa     300
gggaccaagg tggaaatcaa a                                               321
```

METHODS OF MAKING ACTIVE ANTIBODIES FROM BIOLOGICAL FLUIDS

CROSS-REFERENCE TO RELATED APPLICATIONS

This application claims the benefit of U.S. Provisional Appl. No. 62/341,211, filed May 25, 2016, the contents of which are hereby incorporated by reference in their entirety.

STATEMENT OF FEDERALLY SPONSORED RESEARCH AND DEVELOPMENT

This invention was made with government support under the Grant Number AI110259 awarded by the National Institutes of Health and Grant Number 1I01BX002358 awarded by the U.S. Department of Veterans Affairs. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 23,115 Byte ASCII (Text) file named "Sequence_Listing_ST25.txt," created on May 25, 2017.

FIELD OF THE INVENTION

The invention relates to infectious disease and to methods of discovering therapeutics to treat and prevent infections.

BACKGROUND OF THE INVENTION

HIV is an integrating retrovirus that rapidly establishes chronic infection in CD4+ T cells. This fundamental characteristic means that inhibition of HIV infection depends in large measure on the specificities and activities of humoral responses against HIV envelope proteins (gp120 and gp41) that drive viral attachment and entry.

Humoral anti-envelope responses in some HIV-infected persons comprise neutralizing activity against diverse HIV strains. J. F. Scheid et al., *Nature* 458, 636-640 (2009); M. D. Simek et al., *J Virol* 83, 7337-7348 (2009); L. M. Walker et al., *PLoS Pathog* 6, e1001028 (2010); M. M. Sajadi et al., *J Acquir Immune Defic Syndr* 57, 9-15 (2011); M. M. Sajadi et al., *J Infect Dis* 213, 156-164 (2016). Relatively little is known about polyclonal responses that support titers of broadly HIV-neutralizing plasma antibodies in HIV-infected persons. To date, efforts to address this question have relied on affinity fractionation, antigen depletion or infectivity analyses using viral envelopes with targeted mutations. D. N. Sather et al., *Vaccine* 28 Suppl 2, B8-12 (2010); Y. Li et al., *J Virol* 83, 1045-1059 (2009); A. K. Dhillon et al., *J Virol* 81, 6548-6562 (2007). Although highly useful, this method focuses only on the neutralizing species and does not fully define the background milieu of the ongoing, polyclonal anti-envelope humoral response. Memory B cell-derived neutralizing mAbs undoubtedly provide important information regarding structural and functional aspects of epitope-paratope interactions. However, memory B cell-derived mAbs may not correspond to circulating antibodies and/or may not exist at relevant, functional levels (Y. Guan et al., *Proc Natl Acad Sci USA* 106, 3952-3957 (2009)). Additionally, the neutralization profiles of the mAbs, as measured by in vitro assays, may only partially resemble the plasma neutralizing activities of the source subjects at the time they were identified. M. H. Scheid et al., *Nature* 458, 636-640 (2009); L. M. Walker et al., *Science* 326, 285-289 (2009); L. M. Walker et al., *Nature* 477, 466-470 (2011). Thus, the interrelationships between broadly neutralizing monoclonal antibodies and circulating anti-HIV envelope humoral repertoires are mostly established by indirect evidence.

There have only been limited studies until now of deconvolution of circulating polyclonal responses using proteomics. A proteomics strategy has been used recapitulate the CDR3 repertoires in rabbits immunized against *Concholepas* hemocyanin, or in humans vaccinated with tetanus toxoid. Y. Wine et al., *Proc Natl Acad Sci USA* 110, 2993-2998 (2013); J. J. Lavinder et al., *Proc Natl Acad Sci USA* 111, 2259-2264 (2014). However, a lingering caveat for the operation is that the assembled Ig species may not accurately reflect authentic heavy and light chain pairings. Recently, Williams et al. used a similar approach to identify antibodies from the memory B cell pool that closely matched circulating antibody. L. D. Williams et al., *Science Immunology* in press, (2017). While this technique worked to identify new mAbs, there is still a question as to whether the mAbs were actually in circulation as they were matched to the memory B cell pool.

Previously we described a cohort of subtype B-infected, Elite Controllers, not on antiretroviral therapy, who exhibit persistent titers of very broad and potent neutralizing antibodies. M. M. Sajadi et al., *J Infect Dis* 213, 156-164 (2016); M. M. Sajadi et al., *J Virol* 86, 5014-5025 (2012). Importantly, multiple subjects in this cohort harbored broad and potent neutralizing activities with highly shared biochemical determinants, such as basic isoelectric points (pI) and specificities for binding epitopes on free gp120. M. M. Sajadi et al., *J Acquir Immune Defic Syndr* 57, 9-15 (2011); M. M. Sajadi et al., *J Infect Dis* 213, 156-164 (2016); M. M. Sajadi et al., *J Virol* 86, 5014-5025 (2012).

There is a significant need to develop new therapeutics and methods to treat and prevent infectious diseases in patients.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

In one aspect, the invention provides a method of making an antibody by identifying a circulating antibody with activity from a subject comprising i) subjecting a biological fluid selected from blood, plasma, serum and combinations thereof from the subject to one or more rounds of affinity chromatography to purify the circulating antibody;

ii) optionally further subjecting the circulating antibody to isoelectric focusing to purify the circulating antibody based on charge;

iii) testing the purified circulating antibody for activity;

iv) digesting the purified circulating antibody from parts i) or ii) to create an antibody fragment;

v) subjecting the antibody fragment to mass spectrometry to generate a mass assignment and a deduced amino acid sequence of the antibody fragment;

vi) comparing the deduced amino acid sequence with an amino acid sequence of an antibody generated from the subject's B-cells to identify an antibody sequence that matches the deduced amino acid sequence;

vii) generating an antibody comprising light chain and heavy chain CDR sequences of the B-cell antibody that matches the deduced amino acid sequence of part vi); and viii) testing the antibody of part vii) for activity.

In another aspect, the invention provides a method of identifying a circulating antibody with activity from a subject comprising i) subjecting biological fluid selected from blood, plasma, serum and combinations thereof from the subject to one or more rounds of affinity chromatography to purify the circulating antibody;

ii) optionally further subjecting the circulating antibody to isoelectric focusing to purify the circulating antibody based on charge;

iii) testing the purified circulating antibody for activity;

iv) digesting the purified circulating antibody from parts i) or ii) to create an antibody fragment;

v) subjecting the antibody fragment to mass spectrometry to generate a mass assignment and a deduced amino acid sequence of the antibody fragment; and vi) comparing the deduced amino acid sequence with an amino acid sequence of an antibody generated from the subject's B-cells to identify an antibody sequence that matches the deduced amino acid sequence.

In another aspect, the invention provides a method of treating a disease or condition in a subject, comprising administering to the subject an effective amount of an antibody prepared in accordance with the methods of the invention.

In another embodiment, the invention provides a method of treating or preventing HIV, comprising administering to the subject an effective amount of an antibody of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 9. Comparison of characteristics of antibodies derived from plasma and fractionated antibody samples. Samples tested for pI (isoelectric point of mAb or IEF fraction) and ELISA. ELISA was done against monomeric BaL gp120, monomeric gp120 with the D368R mutation abrogating binding of CD4BS antibodies, FLSC (Full-length single china, a fusion protein of gp120 and CD4), and YU2 core (core protein of YU2 envelope lacking V1, V2, and V3 loops): negative <0.12, 1+=0.12-0.5; 2+=0.5-1.0; 3+=1.0-1.5; 4+=>1.5. Neutralization refers to presence or absence of neutralization breadth against a Tier 2/3 panel (all mAbs underwent testing, and IEF fraction results are from previously performed experiments with the same panel).

*These antibodies did not have binding to Bal-gp120 on ELISA, but were able to bind BaL-gp120 when conjugated to agarose beads. Thus, they could have been matched in our algorithm by direct sequencing once eluted from the column and/or matched by the basis of homology to related antibodies that can bind gp120.

Figure 10:
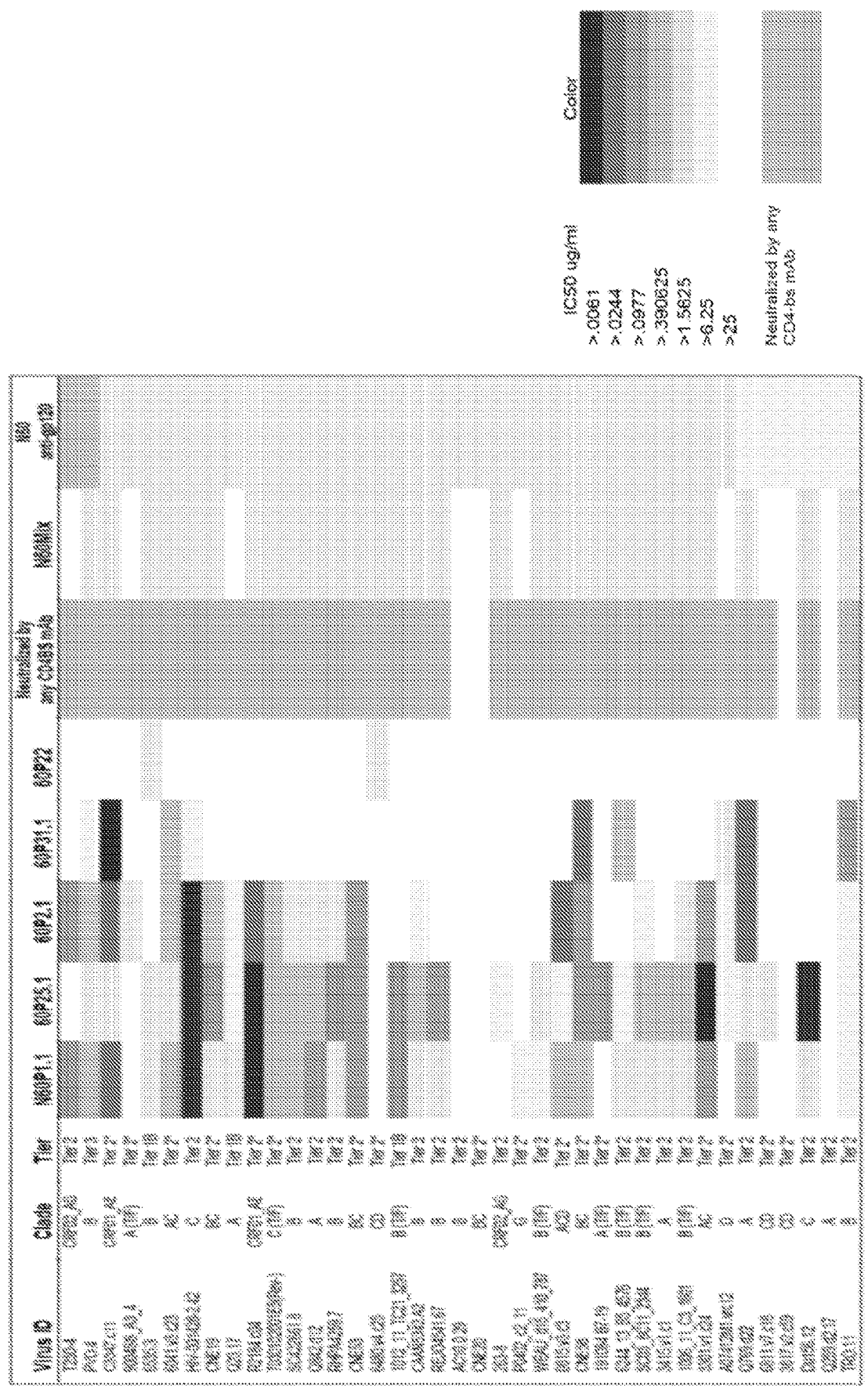
Figure 10:
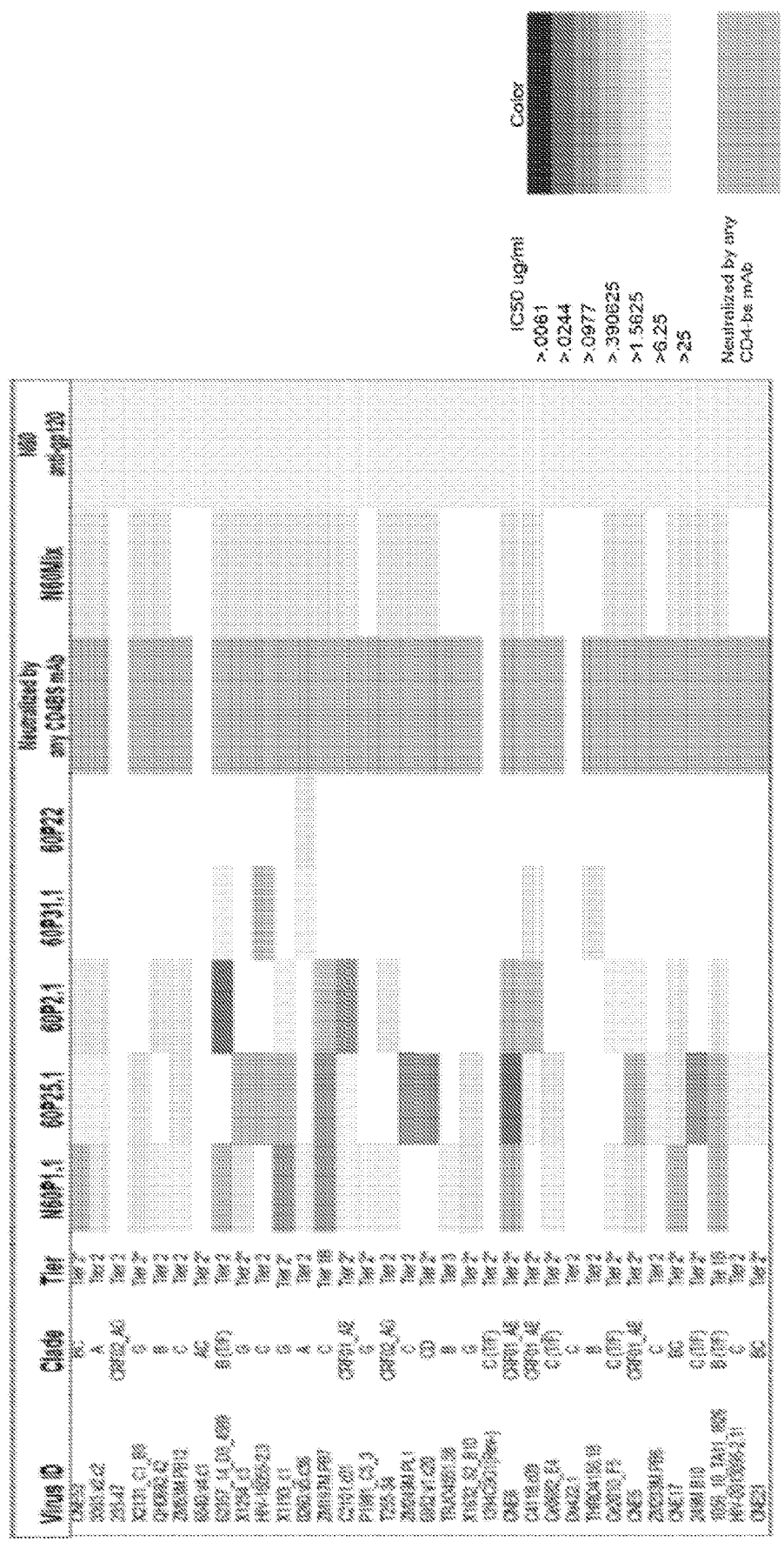

FIG. 10. Neutralization activity plasma derived anti-Env antibodies (alone and in combination). A panel of HIV-1 viral envelope strains (individual viruses listed on the left column) that were sensitive to the parent sample NVS60 gp120-Ig were tested against all CD4-BS antibodies. IC50 values are color-coded according to the color key on the left: the greater the neutralization, the darker red the color; grey represents no neutralization (IC50>25 ug/ml). Individually, the CD4-BS accounted for 89% of the neutralization breadth of the parent sample. One family of CD4i were able to neutralize one the mAbs the CD4-BS mAbs could not neutralize (not shown). Thus, the mAbs, individually, were able to account for 90% of the neutralization breadth. An equimolar mix of the mAbs called N60mAb mix (CD4-BS, CD4i, and variable loop antibodies at equimolar concentrations) neutralized 68.5% of the pseudoviruses. IC50=Inhibitory Concentration 50.

Figure 11:
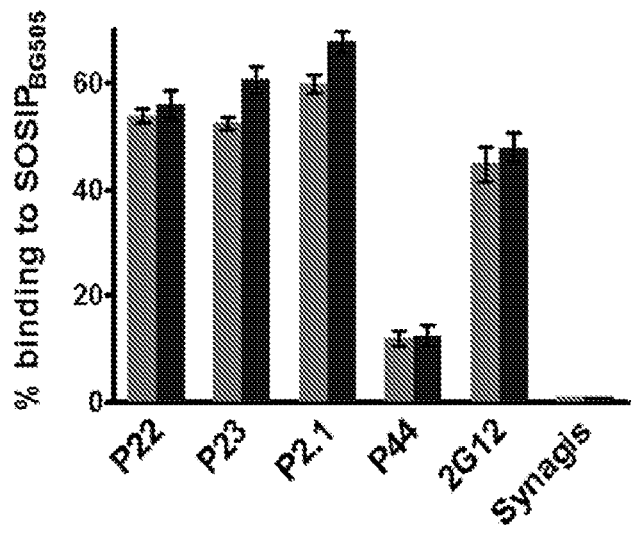
Figure 11:
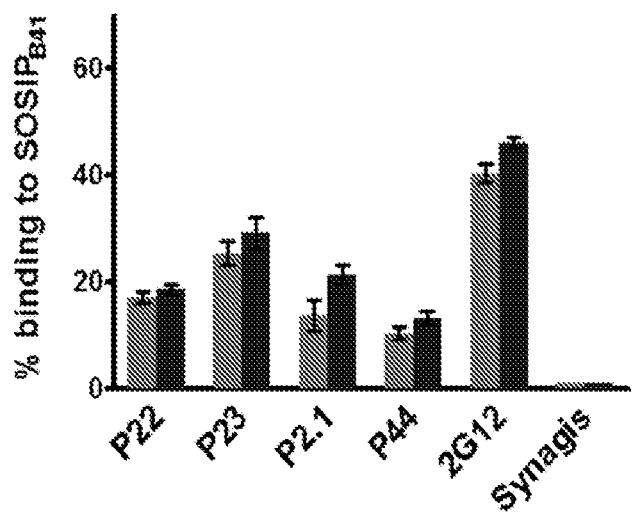

FIG. 11. Percent binding of CD4-BS mAbs to trimers by fluorescence correlation spectroscopy. Alexa-647 labeled mAbs Ab were tested for binding to trimers treated at 37° C. Percent binding of CD4-BS mAbs, G12, and negative control Synagis to Sosip B41 (Clade B) and Sosip BG505 (Clade A/E) are shown. mAbs tested at of concentrations 1 ug/ml (grey bar), 5 ug/ml (blue bar), with Sosip concentration at 50 ug/ml. All CD4-BS mAbs demonstrate binding to both trimers, while the Synagis control does not.

Figure 12:
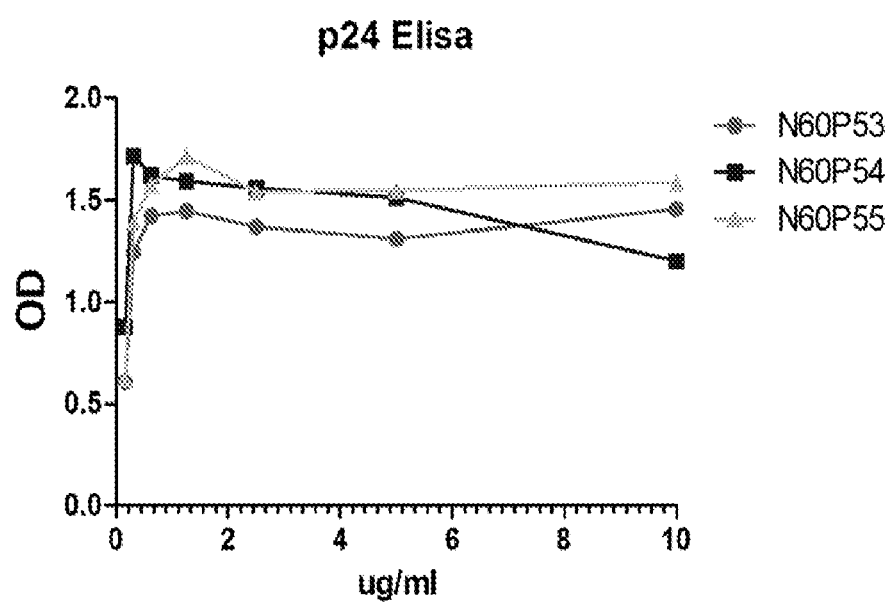

FIG. 12. Elisa binding of N60P53, N60P54, and N60P55 to HIV-1 p24. Elisa plates coated with HIV-1 IIIB p24 overnight, and mAbs tested starting at 10 ug/ml with 1:2 dilution. All 3 mAbs demonstrate strong binding to p24 at all concentration tested.

Figure 13A:
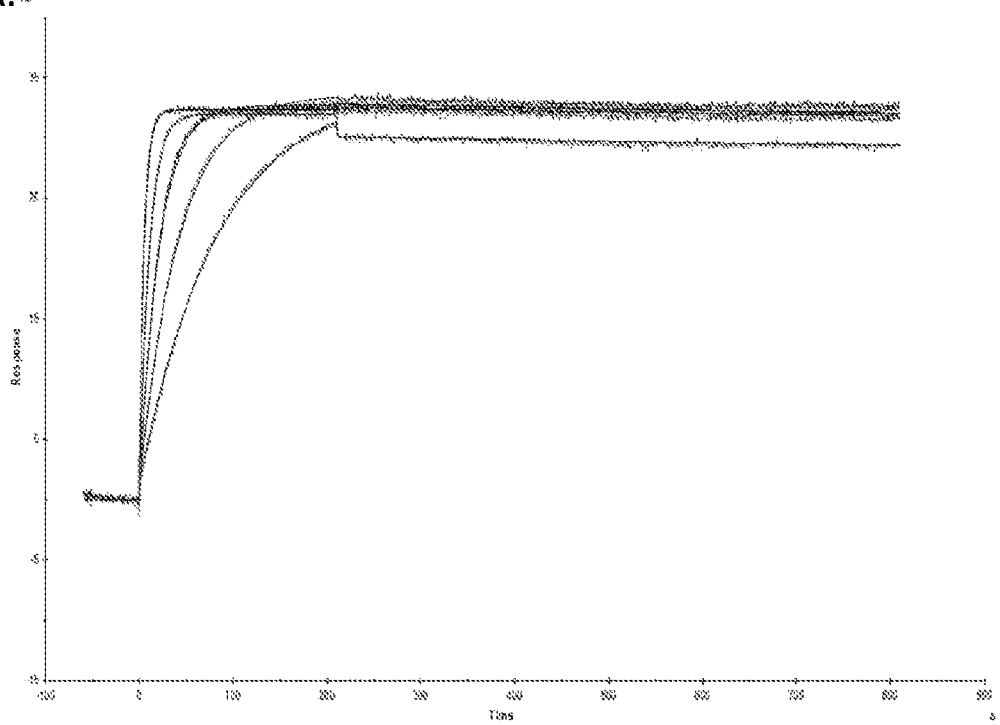
Figure 13B:
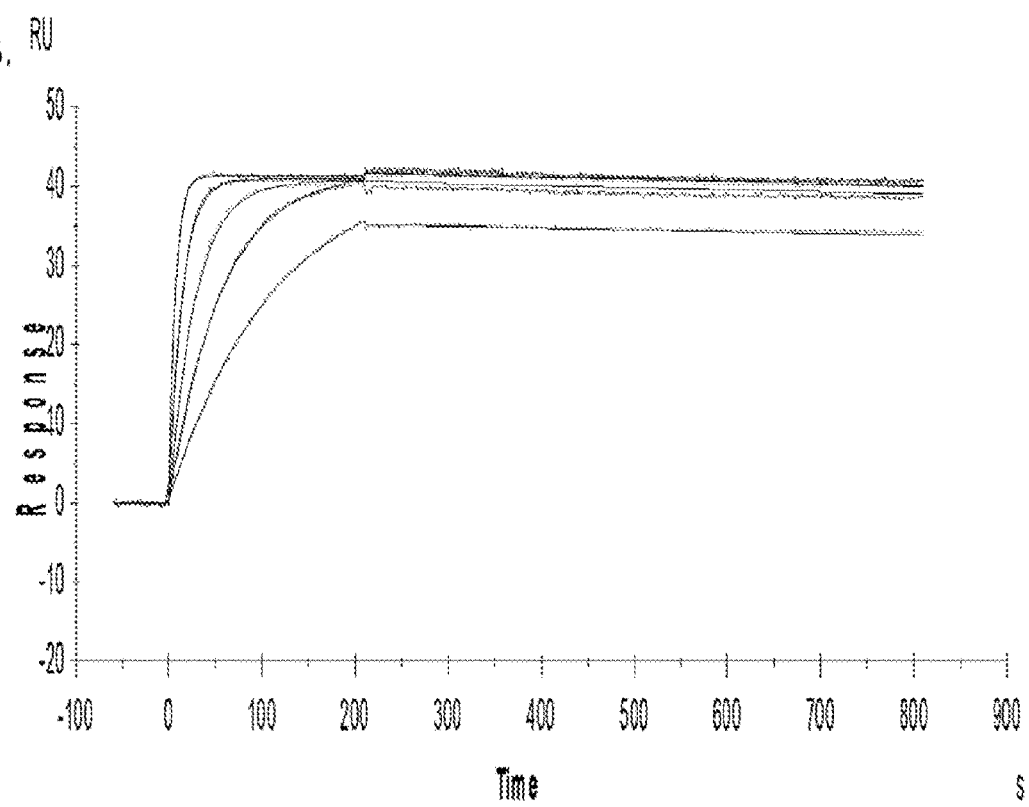
Figure 13C:
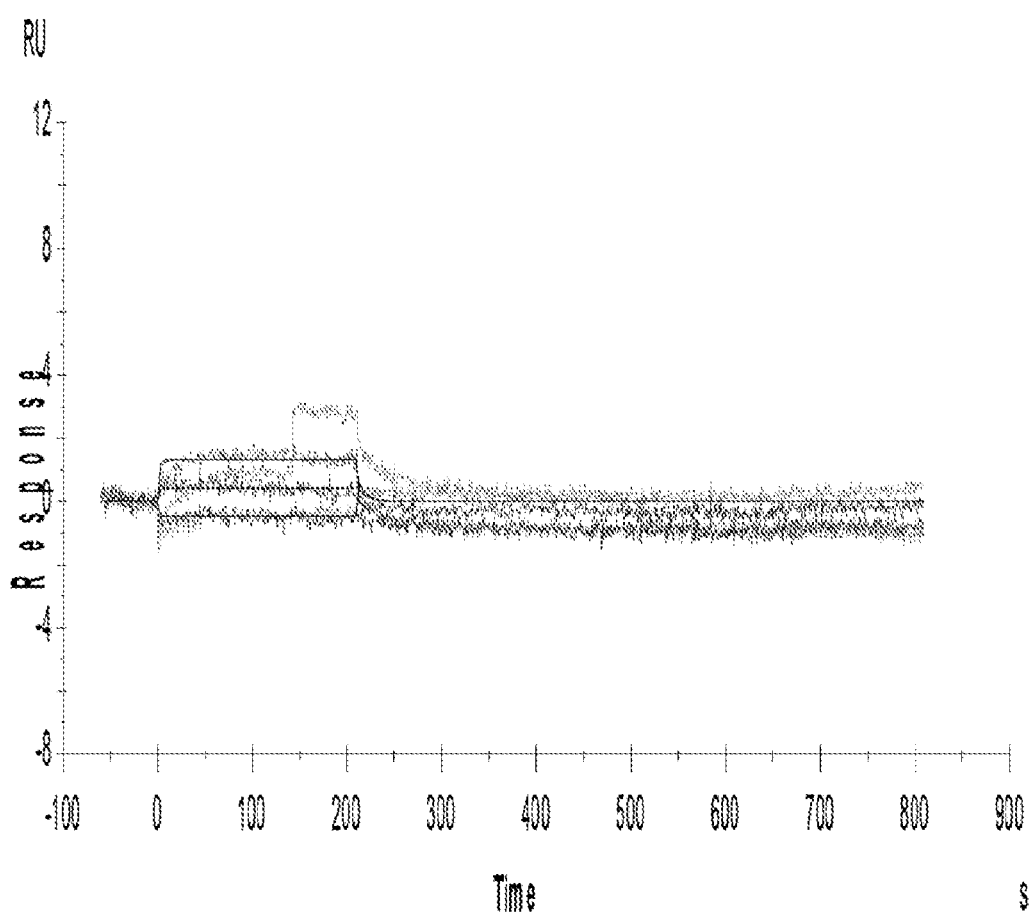

FIG. 13. Surface Plasmon Resonance (SPR) analysis of anti-p24 mAbs. One mAb from each of the two families of anti-p24 mAbs (N60P53 and N60P55) were chosen to analyze binding of HIV-1 IIIB p24 recombinant protein. Surface Plasmon Resonance (SPR) analysis of each mAb binding to p24. Sensorgrams were obtained at room temperature for each mAb immobilized on a Protein A chip with 0-200 nM concentrations of p24 passed over the chip. A) Binding of mAb N60P53 to p24: $k_a$, $k_d$, and $K_D$ were 9.536E+5, 3.806E−5, and 3.991E−11, respectively. B) Binding of mAb N60P55 to p24: $k_a$, $k_d$, and $K_D$ were 7.146E+5, 6.553E−5, 9.170E−11, respectively. C) Binding of Synagis (an anti-RSV mAb used as negative control) to p24. No binding was observed, and thus $k_a$, $k_d$, and $K_D$ could not be calculated. $k_a$=association rate constant [M−1 s−1]; $k_d$=dissociation rate constant [s−1]; $K_D$=the equilibrium dissociation constant [M].

Figure 14:
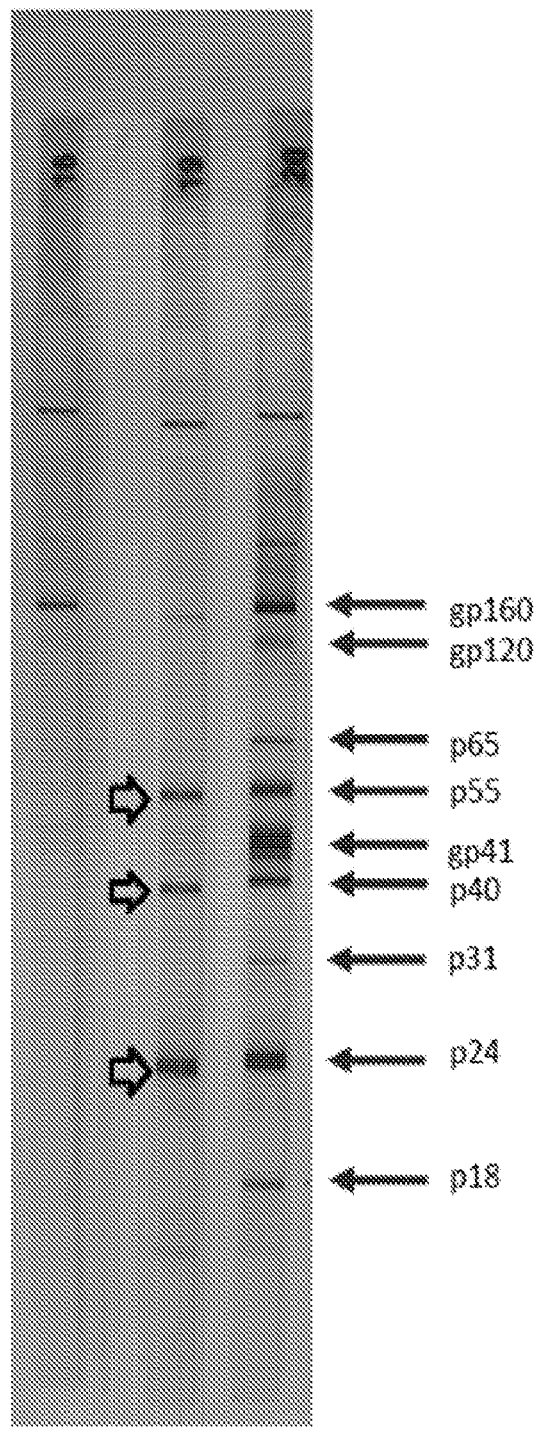

FIG. 14. HIV-1 Western Blot demonstrating binding of N60P53 to HIV-1 p24 and its precursors (p40 and p55). 10 ug/ml of the mAb N60P53 was tested by HIV-1 Western Blot. Controls included a negative strip (strip 16), mAb N60P24 (Strip 19), and N60 serum (Strip 20). The positioning of the various HVI01 proteins are shown in Strip 20 with the red arrows. The mAb N60P54 has strong bands (hollow black arrows) at bands p24, and its precursors (p40 and p55), demonstrating specific binding to HIV-1 p24.

Figure 15A:
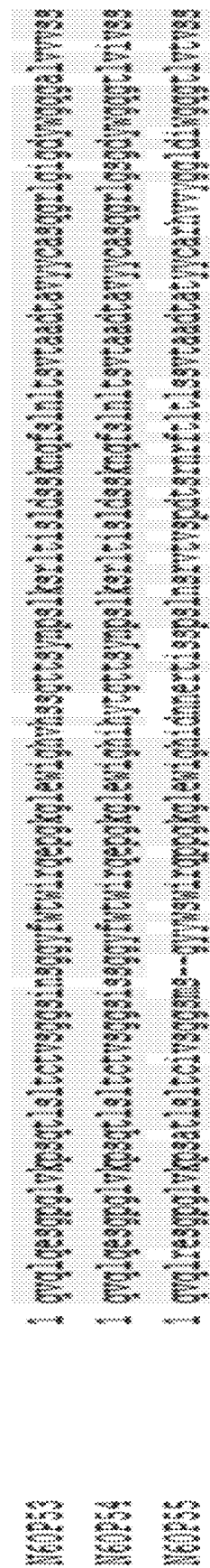
Figure 15B:
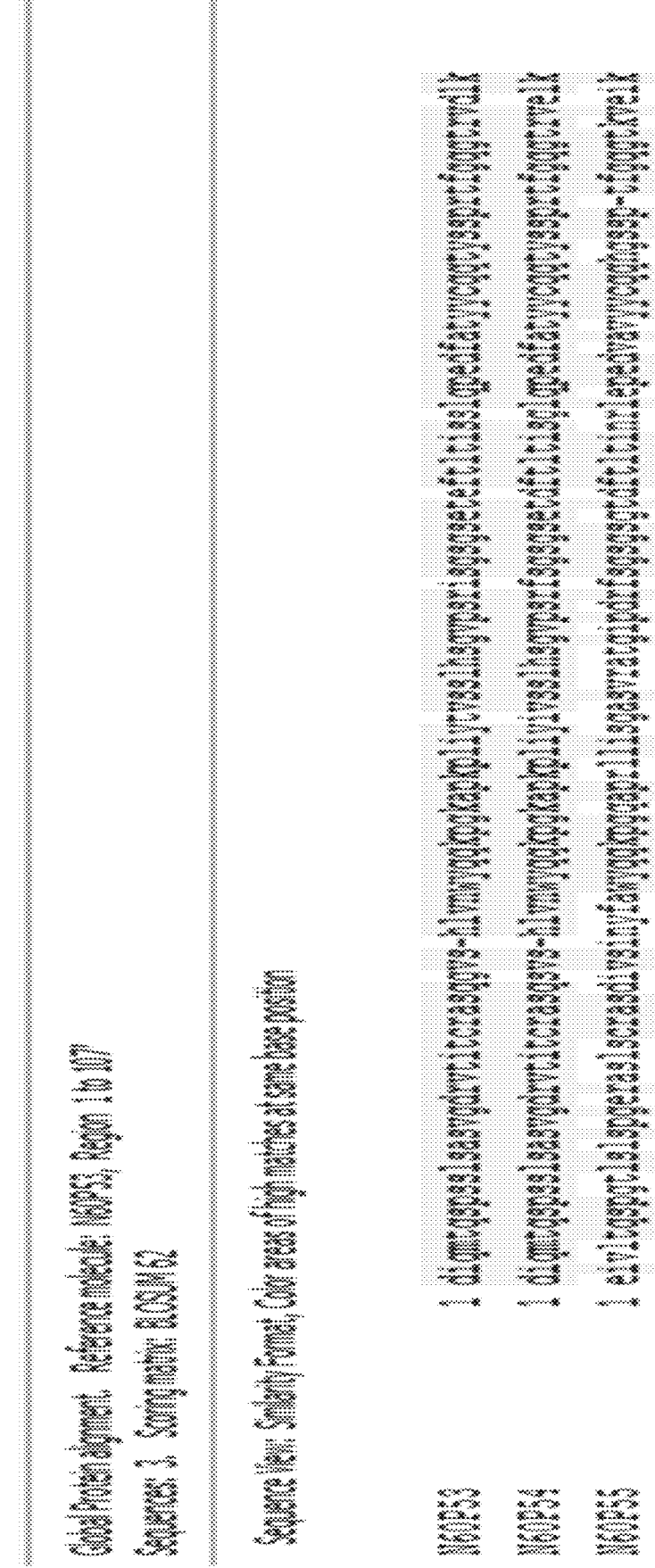

FIG. 15. Heavy and light chain amino acid sequences for anti-p24 mAbs. Protein sequences of N60P53, N60P54, and N60P55 heavy and light chains are shown (Panel A and B, respectively). N60P54 has 96% heavy chain and 94% light chain homology with N60P53, while N60P55 has 66% heavy chain and 58% light chain homology with N60P53.

DETAILED DESCRIPTION OF THE INVENTION

The present invention is based on the discovery that broadly neutralizing antibody responses from biological fluid such as plasma in certain infected individuals, such as an individual with HIV, can be used to guide the development of effective therapies to infectious disease.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

In some aspects, the practice of the present invention employs various techniques of molecular biology (including recombinant techniques), microbiology, cell biology, biochemistry and immunology. See, e.g., Sambrook et al. *Molecular Cloning: A Laboratory Manual*, 2$^{nd}$ edition (1989); *Current Protocols in Molecular Biology* (F. M. Ausubel et al. eds. (1987)); the series *Methods in Enzymology* (Academic Press, Inc.); PCR: *A Practical Approach* (M. MacPherson et al. IRL Press at Oxford University Press (1991)); PCR 2: *A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "an antibody" includes a plurality of antibodies, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

In one embodiment, the invention provides a method of identifying a circulating antibody with activity from a subject comprising
  i) subjecting biological fluid selected from blood, plasma, serum and combinations thereof from the subject to one or more rounds of affinity chromatography to purify the circulating antibody;
  ii) optionally further subjecting the circulating antibody to isoelectric focusing to purify the circulating antibody based on charge;
  iii) testing the purified circulating antibody for activity;
  iv) digesting the purified circulating antibody from parts i) or ii) to create an antibody fragment;
  v) subjecting the antibody fragment to mass spectrometry to generate a mass assignment and a deduced amino acid sequence of the antibody fragment; and
  vi) comparing the deduced amino acid sequence with an amino acid sequence of an antibody generated from the subject's B-cells to identify an antibody sequence that matches the deduced amino acid sequence.

In another embodiment, the invention provides a method of making an antibody by identifying a circulating antibody with activity from a subject comprising
  i) subjecting biological fluid selected from blood, plasma, serum and combinations thereof from the subject to one or more rounds of affinity chromatography to purify the circulating antibody;
  ii) optionally further subjecting the circulating antibody to isoelectric focusing to purify the circulating antibody based on charge;
  iii) testing the purified circulating antibody for activity;
  iv) digesting the purified circulating antibody from parts i) or ii) to create an antibody fragment;
  v) subjecting the antibody fragment to mass spectrometry to generate a mass assignment and a deduced amino acid sequence of the antibody fragment;
  vi) comparing the deduced amino acid sequence with an amino acid sequence of an antibody generated from the subject's B-cells to identify an antibody sequence that matches the deduced amino acid sequence;

vii) generating an antibody comprising light chain and heavy chain CDR sequences of the B-cell antibody that matches the deduced amino acid sequence of part vi); and viii) testing the antibody of part vii) for activity.

The activity of the antibody can include, e.g., binding to an antigen, antibody dependent cellular phagocytosis, antibody dependent cell-mediated toxicity, and neutralization activity.

In some embodiments, the circulating antibody has activity against a pathogen, which is not necessarily limiting. In some embodiments, the pathogen is selected from the group consisting of *Bacillus anthracis, Bordetella pertussis, Borrelia* spp., *Brucella* spp., *Chlamydia* spp., *Clostridium botulinum, Clostridium tetani, Corynebacterium diphtheriae, Enterobacterеciae, Escherichia coli, Haemophilus influenza, Helicobacter pylori, Hemophilus* spp., *Klebsiella* spp., Streptococcus pneumonia, *Legionella pneumophila, Listeria monocytogenes, Mycobacterium tuberculosis, Mycoplasma* spp., *Neisseria gonorrhoeae, Neisseria meningitidis, Pseudomonas* spp., *Ricketsia* spp., *Salmonella* spp., *Shigella* spp., *Staphylococcus* spp., *Streptococci* spp., *Vibrio cholera, Yersinia* spp., *Adenovirus* species, CCHF virus, Cytomegalovirus, Dengue virus, Ebola virus, Epstein-Barr virus, Hepatitis A virus, Hepatitis B virus, Herpes simplex viruses, HIV, HTLV, Human Herepes virus 6-8, Influenza virus, Measles virus, Mumps virus, Polio virus, Rabies virus, Rubella virus, SARS and associated coronaviruses, Respiratory Syncytial virus, Varicella Zoster virus, West Nile Virus, Yellow Fever virus, Zika virus, *Plasmodium* spp., and agents of endemic mycoses.

In some embodiments, the subject has circulating antibody with activity that is capable of neutralizing the pathogen. In some embodiments, the neutralizing response by the subject against the infection is contributed by a plurality of circulating antibodies with activity that have different amino acid sequences. In some embodiments, the neutralizing response by a single antibody is about 30% of the neutralizing response in the subject, about 40% of the neutralizing response, about 50% of the neutralizing response, about 60% of the neutralizing response, about 70% of the neutralizing response, about 80% of the neutralizing response, about 90% of the neutralizing response, about 95% of the neutralizing response, about 99% of the neutralizing response, or about 100% of the neutralizing response. In some embodiments, in the case of HIV, neutralization testing can be performed using a luciferase-based assay in TZM.b1 cells as previously described. See, e.g., M. M. Sajadi et al., *J Acquir Immune Defic Syndr* 57, 9-15 (2011).

In some embodiments, the subject is infected with HIV. In some embodiments, the subject is an "elite controller" of HIV, which is a recognized term applied to a small group of HIV-positive individuals who maintain HIV-1 viral loads <400 copies/ml even in the absence of any treatment (M. M. Sajadi et al., *J Acquir Immune Defic Syndr* 50, 403-408 (2009); M. M. Sajadi et al., *AIDS* 21, 517-519 (2007). In some embodiments, the circulating antibody binds an HIV antigen. In some embodiments, the antigen is selected from the group consisting of gp120, p24, gp41, p31, p17, p55, RT, rev, nef, vpu, tat and combinations thereof. In some embodiments, the circulating antibody binds a gp120 epitope selected from the group consisting of a CD4 binding site, a CD4 induced epitope, and a V3 epitope. In some embodiments, the subject exhibits a neutralizing polyclonal antibody response that comprises circulating antibodies against gp120 epitopes comprising a CD4 binding site, a CD4 induced epitope, and a V3 epitope.

In some embodiments, the circulating antibody with activity binds free gp120. In some embodiments, the circulating antibody is capable of neutralizing a panel of HIV viruses. In some embodiments, the HIV panel comprises Tier 1 viruses, Tier 2 viruses, Tier 3 viruses and combinations thereof. In some embodiments, the circulating antibody is capable of neutralizing one or more HIV viruses as shown in Tables 1 and 2. In some embodiments, the circulating antibody is capable of neutralizing HIV virus at a concentration of <50 μg/ml, 25 μg/ml, 15 μg/ml, 10 μg/ml, 5 μg/ml or 1 μg/ml.

The circulating antibody isotype class and subclass is not particularly limiting. Five major antibody classes have been identified in placental mammals: IgA, IgD, IgE, IgG and IgM. This classification is based on differences in amino acid sequence in the constant region (Fc) of the antibody heavy chains. IgG and IgA are further grouped into subclasses (e.g., in human IgG1, IgG2, IgG3, IgG4, IgA1 and IgA2) based on additional small differences in the amino acid heavy chain sequences. Based on differences in the amino acid sequence in the constant region of the light chain, immunoglobulins can be further sub-classified by determination of the type of light chain (kappa light chain or lambda light chain). In some embodiments, the circulating antibody with activity is an IgG antibody. In some embodiments, the circulating antibody with activity is an IgG1, IgG2, IgG3, or IgG4 antibody. In some embodiments, the circulating antibody with activity has a kappa light chain. In some embodiments, the circulating antibody has a lambda light chain. In some embodiments, the circulating antibody is an IgG1 kappa chain antibody. In some embodiments, the circulating antibody is an IgG1 lambda chain antibody. In some embodiments, the circulating antibody comprises less than 10% of the circulating IgG in the subject. In some embodiments, the circulating antibody comprises less than 9%, 8%, 7%, 6%, 5%, 4%, 3%, 2%, or less than 1% of the circulating IgG in the subject.

In accordance with the invention, the biological fluid selected from blood, plasma, serum and combinations thereof from the subject is subjected to one or more rounds of affinity purification to purify the circulating antibody. Affinity chromatography is a method of separating biochemical mixtures based on highly specific interactions between antigen and antibody, enzyme and substrate, or receptor and ligand. It can be used to purify biological molecules within a mixture by exploiting molecular properties. In some embodiments, the affinity chromatography comprises purifying circulating IgG antibody using protein A. In some embodiments, the affinity chromatography comprises purifying circulating antibody using an antigen. In some embodiments, the affinity chromatography comprises purifying circulating IgG1 kappa chain antibodies. In some embodiments, the kappa chain antibodies are purified using Protein L. In some embodiments, the affinity chromatography comprises purifying circulating IgG1 lambda chain antibodies.

In some embodiments, the biological fluid selected from blood, plasma, serum and combinations thereof is fractioned into IgG1 κ and IgG1λ antibodies, which can be achieved by a series of purifications, e.g., plasma->protein A column->IgG1 column->kappa and lambda columns. In some embodiments, the biological fluid selected from blood, plasma, serum and combinations thereof is fractioned into anti-gp120 κ and anti-gp120λ antibodies using a series of purifications, e.g., plasma->protein A column->gp120 column->kappa and lambda columns, or fractioned into anti-gp120 antibodies (plasma->protein A column->gp120 column). Similar strategies can be employed using different antigens.

In some embodiments, affinity purified and fractioned antibody can be subjected to isoelectric focusing to purify the circulating antibody further based on charge. In some embodiments, the isoelectric focusing is free flow electrophoresis (FFE). See, e.g., BD Free Flow Electrophoresis System (BD, Franklin Lakes, N.J.). In some embodiments, the circulating antibody has a PI between 6 and 11.

The purified antibody is tested for activity prior to mass spectrometry to identify fractions that have activity. In some embodiments, the purified circulating antibody that tests positive for activity (e.g., in a binding or functional assay) is subjected to isoelectric focusing. In some embodiments, the purified circulating antibody is tested by ELISA for reactivity against an antigen. In some embodiments, the antigen is selected from the group consisting of BaL-gp120 monomer, BaL-gp120 monomer with D368R mutation to abrogate CD4-BS binding, Yu2 gp120 core with V3 loop, Yu2 gp120 core, full length CD4-induced gp120 in which the CD4 binding site is occupied.

In some embodiments, when the purified circulating antibody from affinity purification steps or isoelectric focusing tests positive in a binding or functional assay, it is digested to create antibody fragments and subjected to mass spectrometry to generate a mass assignment and a deduced amino acid sequence of the antibody fragment.

In some embodiments, the circulating antibody is digested with a protease to create peptide fragments. In some embodiments, the circulating antibody is digested with a protease(s) selected from the group consisting of trypsin, chymotrypsin plus Glu-C, and combinations thereof and the fragments are subjected to mass spectrometry (MS). In some embodiments, the mass spectrometry is LC-MS.

The ion source for MS is not limiting. For instance, matrix assisted laser desorption (MALDI) and electrospray ionization (ESI) are two techniques that allow for the transfer of large nonvolatile molecules into the gas phase. In MALDI, a low photon absorbing matrix is added to the sample prior to ionization. A laser is then used to irradiate the sample and desorb high-mass biomolecular ions. The precise nature of the MALDI ionization process is still largely unknown. For instance, actual ionization of the peptide will be dependent upon the incorporation of the peptides into the crystals, the likelihood of capturing and/or retaining a proton during the desorption process, and other factors such as suppression effects in peptide mixtures.

In ESI large, multiply charged ion are generated by transporting the analyte solution through a capillary needle that is maintained at a desired voltage relative to ground.

Other ion sources known in the art can be employed with the present embodiments. For instance, it is within the scope of the embodiments that electrospray ionization (EI), fast atom ion bombardment (FAB), chemical ionization (CI), atmospheric pressure photon ionization (APPI), atmospheric pressure chemical ionization (APCI), atmospheric pressure matrix assisted laser desorption ionization (AP-MALDI), and other ion sources can be employed. The ion sources can be under vacuum or at atmospheric pressure absent a vacuum. The ion sources can also be nano size if desired. Any combination of ion source, ion focusing or separation device and detector can be employed with the present embodiments.

Various mass spectrometers have been developed and can be employed with the present embodiments. Mass spectrometers detect the ions or fragments that are produced by the ion sources. Essentially, all mass spectrometers measure the mass-to-charge ratio of analytes such as biomolecules, peptides, proteins, or peptide fragments. Separations are often accomplished using one or more different techniques. For instance, separations can be accomplished using time of flight (TOF MS), separation by quadrupole electric fields, or separation by ion trapping. For structural analysis of various biomolecules or peptides mass spectrometry separations can be accomplished in MS mode or MS/MS where one or more techniques are used in tandem. For instance, both MALDI and ESI can be coupled with one or more of these techniques to accomplish separations. In a typical MALDI/TOF experiment, analytes are deposited on a surface and then irradiated by a laser to produce an "ion plume". The ions then are accelerated to a fixed amount of kinetic energy and directed down a flight tube. The various ions have differing velocities since they differ in size and mass. Once at the end of the flight tube the ions are then reversed or reflected using a reflector prior to being detected by a detector. Other ion sources, detectors and source can be employed with the embodiments of the present invention. For instance, mass spectrometry systems can comprise MALDI, TOF, TOF/TOF, AP-MALDI, ion trap, quadrupole, triple quadrupole, FTICR, chemical ionization, and electrospray ionization. Other ion sources, detectors and device known in the art can be employed with the present embodiments.

In accordance with the invention, the deduced amino acid sequence is compared with an amino acid sequence of an antibody generated from the subject's B-cells to identify an antibody sequence that matches the deduced amino acid sequence. An antibody is then generated that comprises light chain and heavy chain CDR sequences of the B-cell antibody that matches the deduced amino acid sequence of the antibody fragment, followed by testing the antibody for activity, which can include binding to an antigen, antibody dependent cellular phagocytosis, antibody dependent cell-mediated toxicity, and neutralization activity. The antibody can be generated, e.g., by cloning the variable region sequences of the heavy and light chains in frame into immunoglobulin expression vectors that harbor the constant region sequences.

A database of light chain and heavy chain amino acid sequences can be created from the subject's B-cells and used to compare sequences with the deduced amino acid sequence from the purified antibody fragment. The B-cells can be from the subject's blood, lymph node(s) and/or bone marrow. In some embodiments, the B-cells comprise plasmablasts, plasma cells, and memory B cells. In some embodiments, the B-cells comprise bone marrow cells exhibiting a long or short-lived phenotype. In some embodiments, the B-cells comprise circulating plasmablasts having the phenotype IgA$^-$, IgM$^-$, IgD$^-$, CD19+, CD20$^-$, CD27+, and CD38$^{hi}$. In some embodiments, the B-cells comprise bone marrow cells having the phenotype IgA$^-$, IgM$^-$, IgD$^-$, CD19$^+$(or CD19$^-$), CD20$^-$, CD27$^+$, CD38$^{hi}$ and CD138$^-$(or CD138$^+$). In some embodiments, the B-cells comprise unsorted PBMCs, bone marrow CD138– cells, and/or bone marrow CD138+ cells.

The B-cells are analyzed to generate heavy chain and light chain amino acid antibody sequences. In some embodiments, the B-cells are analyzed by single cell PCR and/or deep sequencing. Deep sequencing refers to sequencing a genomic region multiple times which allows for the detection of rare clonal types comprising as little as 1% or less of the original sample. The single cell sequencing method can be performed using any number of known techniques that can amplify and sequence full-length immunoglobulin genes at the level of a single B cell. See, e.g., Y. C. Tan et al., *Clin Immunol* 151, 55-65 (2014), I. Y Ho et al., *J Immunol Methods* 438, 67-70 (2016), R. Murugan et al., *Eur J Immunol,* 45(9):2698-2700 (2015), which is incorporated by reference herein.

In some embodiments, the unsorted PBMCs, bone marrow CD138− cells, and/or bone marrow CD138+ cells are analyzed by deep sequencing to obtain amino acid sequences of the heavy and light chain variable regions. In some embodiments, B-cells comprising Yu2-gp140 reactive memory B-cells, circulating plasmablasts, and CD138−, and CD38hi bone marrow cells are analyzed by single cell sequencing to obtain amino acid sequences of the heavy and light chain variable regions.

The deduced amino acid sequence is compared to the heavy and/or light chain sequences. In some embodiments, an algorithm is used to compare the sequences. In some embodiments, for deep sequencing data, an algorithm can be used based on somatic hypermutation, percent antibody coverage, number of digests found in, frequency of antibody in the database, CDR3/CDL3 length/deletion to identify top-scoring antibody sequences. In some embodiments, the algorithm involves using a scoring system (1 to 3 points) for frequency of antibody found in the repertoire (<0.099 per 1000, 0.1-0.99 per 1000, >1 per thousand), percent coverage of parent antibody strain (<44%, 45-64%, >65%), CDR3 length (10-15, 16-19, <9 or >20), percent amino acid mutation compared to germline (<15%, 16-25%, >26%). In this algorithm, preference was also given for antibodies that were matched in more than one digest, as well as in the bone marrow versus PBMC. For single-cell sequencing, in some embodiments, a different algorithm can be used mainly relying on unique peptides to identify top-scoring antibody sequences. In some embodiments, this algorithm ranks antibodies based on the number of peptides that are unique. Antibodies will typically have a number of peptides that can match it as well as other antibodies that share the same ancestral germline (typically these will be in the framework regions). However, there will also be peptides that will match only one antibody (and its clones) and not others, these are considered to be unique peptides. The more unique peptides an antibody has, the likelier it is that the match is true. Thus, top scoring antibodies can be manufactured and screened for activity.

In another embodiment, the invention provides a method of treating or preventing an infection in a subject, comprising administering to the subject an effective amount of an antibody with activity according to the present disclosure. In some embodiments, the subject has HIV or is at risk of acquiring HIV. In some embodiments, a combination of antibodies with activity are administered. In some embodiments, the antibodies are neutralizing antibodies.

As used herein, an "effective amount" is an amount of an agent or composition that alleviates, totally or partially, the pathophysiological effects of infection or other pathological indication of the invention. Unless otherwise indicated, the agent or composition is administered at a concentration that is a therapeutically effective amount. A therapeutically effective amount can also be an amount that is given prophylactically thereby inhibiting any pathophysiological effects of infection, or other pathological indication of the invention. A therapeutically effective amount will depend upon, for example, subject size, gender, magnitude of the associated disease, condition, or injury, and genetic or non-genetic factors associated with individual pharmacokinetic or pharmacodynamic properties of the administered agent or composition. For a given subject in need thereof a therapeutically effective amount can be determined by one of ordinary skill in the art.

As used herein, "treat" and all its forms and tenses (including, for example, treat, treating, treated, and treatment) refer to both therapeutic treatment and prophylactic or preventative treatment. A subject in need of treatment includes those already with a pathological condition of the invention as well as those in which a pathological condition of the invention is to be prevented.

The terms "inhibiting," "reducing," or "prevention," or any variation of these terms, when used in the claims and/or the specification includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

The subject to be administered the therapeutic agent is not limiting. In some embodiments, the subject a mammal including for example, a dog, cat, monkey, goat, pig, chimpanzee, cow, horse, sheep, rabbit, guinea pig, rat, hamster, mouse, and human. In some embodiments, the subject is a human.

Antibodies

In yet another embodiment, there is provided an antibody that is generated according to the methods of the invention.

In some embodiments, the antibody binds selectively to HIV gp120 protein. In some embodiments, the antibody is N60P23 and has a heavy chain amino acid sequence comprising SEQ ID NO:1 and a light chain amino acid sequence comprising SEQ ID NO:6. In some embodiments antibody N60P23 has a heavy chain nucleotide sequence of SEQ ID NO:5 and a light chain nucleotide sequence of SEQ ID NO:9. In some embodiments, the antibody comprises light chain CDRs comprising SEQ ID NO:7 and 8 and the sequence KSS and heavy chain CDRs comprising SEQ ID NOS:2-4.

In some embodiments, the gp120 antibody is N60P2.1 and has a heavy chain amino acid sequence comprising SEQ ID NO:10 and a light chain amino acid sequence comprising SEQ ID NO:15. In some embodiments antibody N60P2.1 has a heavy chain nucleotide sequence of SEQ ID NO:14 and a light chain nucleotide sequence of SEQ ID NO:17. In some embodiments, the antibody comprises light chain CDRs comprising SEQ ID NO:16 and the sequences EGW and KTS and heavy chain CDRs comprising SEQ ID NOS:11-13.

In some embodiments, the gp120 antibody is N6025.1 and has a heavy chain amino acid sequence comprising SEQ ID NO:18 and a light chain amino acid sequence comprising SEQ ID NO:23. In some embodiments antibody N6025.1 has a heavy chain nucleotide sequence of SEQ ID NO:22 and a light chain nucleotide sequence of SEQ ID NO:26. In some embodiments, the antibody comprises light chain CDRs comprising SEQ ID NO: 24 and 25 and the sequence KSS and heavy chain CDRs comprising SEQ ID NOS:19-21.

In yet another embodiment, there is provided an antibody that binds selectively to HIV p24 protein. In some embodiments, the antibody is antibody N60P53 and has a heavy chain amino acid sequence comprising SEQ ID NO:27 and a light chain amino acid sequence comprising SEQ ID NO:32. In some embodiments antibody N60P53 has a heavy chain nucleotide sequence of SEQ ID NO:31 and a light chain nucleotide sequence of SEQ ID NO:35. In some embodiments, the antibody comprises light chain CDRs comprising SEQ ID NO: 33 and 34 and the sequence TVS and heavy chain CDRs comprising SEQ ID NOS :28-30.

In some embodiments, the p24 antibody is N60P54 and has a heavy chain amino acid sequence comprising SEQ ID NO:36 and a light chain amino acid sequence comprising SEQ ID NO:41. In some embodiments antibody N60P54 has a heavy chain nucleotide sequence of SEQ ID NO:40 and a light chain nucleotide sequence of SEQ ID NO:44. In some embodiments, the antibody comprises light chain CDRs comprising SEQ ID NO: 42 and 43 and the sequence IVS and heavy chain CDRs comprising SEQ ID NOS:37-39.

In some embodiments, the p24 antibody is N60P55 and has a heavy chain amino acid sequence comprising SEQ ID NO:45 and a light chain amino acid sequence comprising SEQ ID NO:50. In some embodiments antibody N60P55 has a heavy chain nucleotide sequence of SEQ ID NO:49 and a light chain nucleotide sequence of SEQ ID NO:53. In some embodiments, the antibody comprises light chain CDRs comprising SEQ ID NO: 51 and 52 and the sequence GAS and heavy chain CDRs comprising SEQ ID NOS :46-48.

The antibodies may be a single chain antibody, a single domain antibody, a chimeric antibody, a Fab fragment, or an IgG.

In still yet another embodiment, there is provided a method of treating or preventing an HIV infection in a subject comprising administering to said subject an antibody as described herein. The method may further comprise administering to said subject one or more additional anti-HIV treatments, which can be given at the same time as said antibody or given before and/or after said antibody. The additional anti-HIV treatment is not limiting. In some embodiments, the additional treatment comprises one or more additional antibodies and/or anti-retroviral therapy.

It will be understood that monoclonal antibodies binding to antigens described herein will have utilities in several applications. These include the production of diagnostic kits for use in detecting and diagnosing disease. In these contexts, one may link such antibodies to diagnostic or therapeutic agents, or use them as capture agents or competitors in competitive assays. Means for preparing and characterizing antibodies are well known in the art (see, e.g., *Antibodies: A Laboratory Manual, Cold Spring Harbor Laboratory,* 1988; U.S. Pat. No. 4,196,265).

In some embodiments, cells can be obtained from previously infected subjects, somatic cells with the potential for producing antibodies, specifically B lymphocytes (B cells), and can be selected for use in the MAb generating protocol. These cells may be obtained from biopsied spleens or lymph nodes, or from circulating blood. The antibody-producing B lymphocytes can be fused with cells of an immortal myeloma cell. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

It also is contemplated that a molecular cloning approach can be used to generate monoclonals. For this, in some embodiments, nucleic acid can be isolated from the cells and the antibody genes obtained by RT-PCR and cloned into an immunoglobulin expression vector.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy® vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies can be generated by subcloning heavy and light chain Fv DNAs from the cloning vector into a second vector, such as a Lonza pConlgG1 or pConK2 plasmid vector, transfected into 293 Freestyle cells or Lonza CHO cells, and antibodies can then be collected and purified from the cell supernatants.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules can comprise fragments (such as F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric or CDR-grafted antibody). In yet a further embodiment, the antibody is a fully human recombinant antibody. Alternatively, one may wish to make more subtle modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

Amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present invention also contemplates isotype modification. By modifying the Fc region to have a different isotype, different functionalities can be achieved. For example, changing to IgGi can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well.

The antibodies of the present invention may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent). It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

In certain embodiments, the antibodies of the present invention may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques can involve, at one level, the crude fractionation of the cellular milieu to polypeptide and non-polypeptide fractions. Having separated the polypeptide from other proteins, the polypeptide of interest can be further purified using chromatographic and/or electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide.

Commonly, complete antibodies are fractionated utilizing agents (i.e., protein A) that bind the Fc portion of the antibody. Antigens can be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

Passive transfer of antibodies, known as artificially acquired passive immunity, generally will involve the use of intravenous or intramuscular injections. Such immunity generally lasts for only a short period of time, but provides immediate protection. The antibodies will be formulated in a carrier suitable for injection, i.e., sterile and syringeable. Thus, the present invention provides pharmaceutical compositions comprising anti-HIV antibodies. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Generally, the ingredients of compositions of the invention are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In order to increase the effectiveness of the antibody therapy of the present invention, it may be desirable to combine this treatment with other agents effective at treating or preventing HIV infections, e.g., anti-retroviral therapy. This process may involve administering to the patient the antibody of the present invention and the other agent(s) at the same time. This may be achieved by use of a single pharmaceutical composition that includes both agents, or by administering two distinct compositions at the same time, wherein one composition includes the antibody of the present invention and the other includes the second agent(s).

The two therapies may be given in either order and may precede or follow the other treatment by intervals ranging from minutes to weeks. In embodiments where the other agents are applied separately, one would generally ensure that a significant period of time did not expire between the time of each delivery, such that the agents would still be able to exert an advantageously combined effect on the patient. In such instances, it is contemplated that one may administer both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the secondary agent will follow general protocols for that drug, taking into account the toxicity, if any. It is expected that the treatment cycles would be repeated as necessary.

In still further embodiments, the present invention concerns immunodetection methods for binding, purifying, removing, quantifying and otherwise generally detecting HIV or an antigen of interest. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In some embodiments, the antibody comprises one or more complementarity determining regions (CDRs) identical to the CDRs of the antibody that matches the deduced amino acid sequence of the antibody fragment from the subject's biological fluid. In some embodiments, the antibody comprises all six of the complementarity determining regions (CDRs) identical to the CDRs of the antibody that matches the deduced amino acid sequence of the antibody fragment from the subject's biological fluid. In some embodiments, the antibody comprises the CDRs of the antibody that matches the deduced amino acid sequence of the antibody fragment from the subject's biological fluid but has been further altered so that it is not identical in amino acid sequence to the natural antibody. The antibodies can be engineered in a number of ways such that they are different from the natural antibody. For example, the antibodies can be engineered to replace or substitute one or more of the heavy or light chain amino acids. In some embodiments, the antibody be modified to replace an IgG1 heavy chain backbone with another IgG heavy chain backbone sequence. In some embodiments, the antibodies can be engineered to have mutations in the VDJ or constant regions. In some embodiments, constant regions can be swapped.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. Identification of Broadly Neutralizing Antibodies from Plasma Against HIV gp120

As set forth in the present disclosure, the plasma neutralizing response of an example subject infected with HIV from the cohort NVS60 (referred to Subject 1 in a previous publication REF) was deconvoluted. Serum antibodies from NVS60 were able to neutralize 90% of 119 multi-clade Tier 2/3 panel of viruses (See Table 1). The duration of such neutralization potency and breadth were confirmed for 5 sequential years of testing with smaller cross-clade panels (Table 2).

The broadly neutralizing plasma response in NVS60 could be affinity purified with free gp120 (Table 1); thus, it did not include major specificities for quaternary gp120 epitopes on envelope trimers or for gp41. M. M. Sajadi et al., *J Acquir Immune Defic Syndr* 57, 9-15 (2011); M. M. Sajadi et al., *J Infect Dis* 213, 156-164 (2016); M. M. Sajadi et al., *J Virol* 86, 5014-5025 (2012). The broadly neutralizing activity could be tracked from the plasma to each subsequent fraction (gp120, IgG1-kappa) (Table 1). The neutralizing response was further restricted to the IgG1 kappa subpopulation of anti-gp120 antibodies (Table 1). M. M. Sajadi et al., *J Acquir Immune Defic Syndr* 57, 9-15 (2011); M. M. Sajadi et al., *J Infect Dis* 213, 156-164 (2016); M. M. Sajadi et al., *J Virol* 86, 5014-5025 (2012). In addition, the original gp120 flow through (antibody that did not bind to monomeric gp120) was tested against a small panel of pseudoviruses to ensure that no major neutralizing activity was in the gp120-FT. In each case, the flow through had lost partial or complete potency against the tested viruses (Table 3).

Our approach towards deconvoluting the NVS60 neutralizing plasma response is based several principles. First, we are interested in the circulating plasma response so our starting material are the circulating antibodies in the plasma and the plasmablasts and plasma cells that produce them (not memory B cells). Furthermore, we introduce a series of affinity purification steps to specifically target the circulating antibody from plasma. At the same time, patient plasmablasts and plasma cells were analyzed with single cell PCR to allow making a database with accurate heavy and light chain pairings. The antibodies are then subjected to mass spectroscopy-based (LC-MS) amino acid sequencing, and analyzed against the patient-specific database to accurately identify the circulating antibodies.

Figure 2:
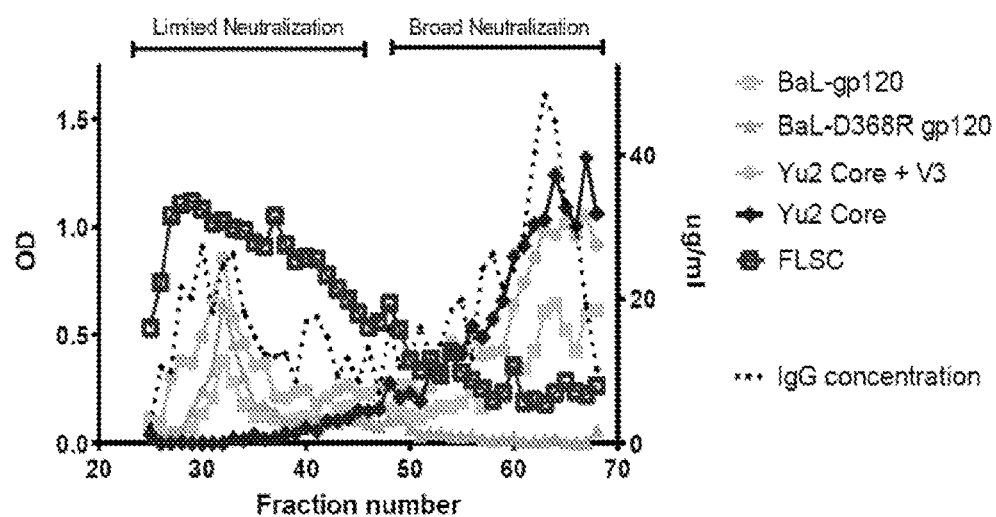
FIG. 2. ELISA reactivity patterns of fractionated IgG from NVS60 with broad HIV neutralizing activity. Anti-gp120 IgG1 kappa (panel A) and lambda (panel B) were fractionated by FFE (see Materials and Methods). Aliquots (0.05 ug) of IgG from each fraction was tested by ELISA for reactivity against the indicated HIV antigens: (BaL-gp120 monomer, BaL-gp120 monomer with the D368R mutation to abrogate CD4-BS binding, Yu2 gp120 core with V3 loop, and Yu2 gp120 core, and full length single chain (FLSC), presenting a full length CD4-induced gp120 structure in which the CD4 binding site is occupied). The X axis represents the IEF fractions (spanning a pH gradient of 6 to 10 from left to right). The Y axis represents ELISA signals expressed as background-corrected OD450 readings/ug IgG. The right Y axis shows IgG concentration of each fraction (ug/ml). Assays were repeated at least twice. Areas of broad and limited neutralization previously identified based on neutralization (ability to neutralize Tier 2 viruses at <10 ug/ml of affinity purified antibody). Y. Li et al., *J Virol* 83, 1045-1059 (2009). Each fraction contains antibodies that can distinguish single epitopes. In panel A, Fractions 55-68 do not bind to D368R envelope mutants but do to the wild-type virus (BaL-gp120). Likewise, Fractions 25-30 and 35-40 in Panel A bind to FLSC (fusion protein between CD4 and gp120) but not monomeric gp120. This strongly suggests a single antibody species (CD4-binding site antibodies and CoReceptor binding site, respectively), as a mixed population of CD4-binding site and non-CD4 binding site antibodies would show some binding to the D368R mutant, and a mixed population of CoReceptor binding site and non-CoReceptor binding site would show binding to the monomer. In Panel B, when the fraction IgG concentrations are compared, the IgG1 anti-gp120 lambda response is almost entirely limited to fractions 28-32, suggesting that one or few antibodies are responsible for the lambda fraction (and by extension up to 60% of the total anti-gp120 response).
Figure 2:
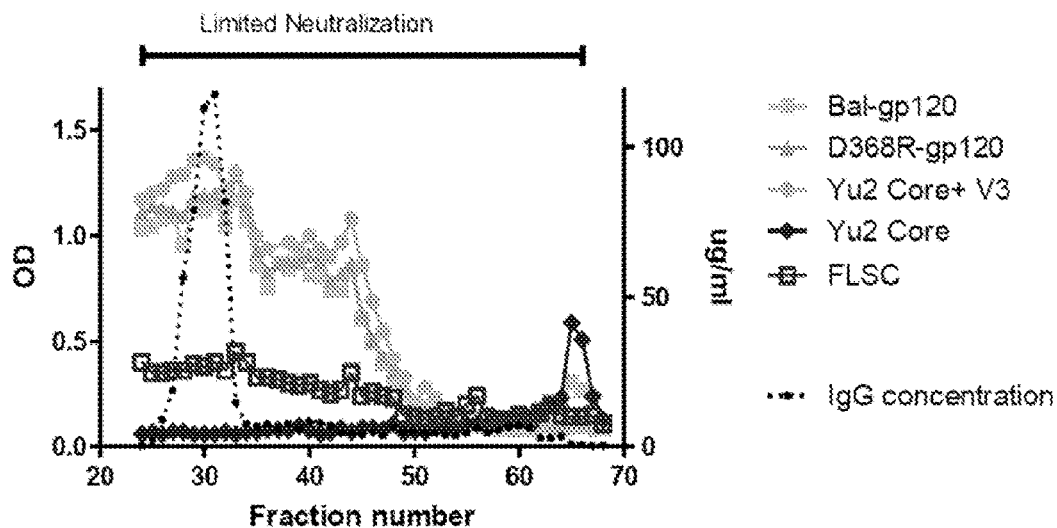
Figure 3:
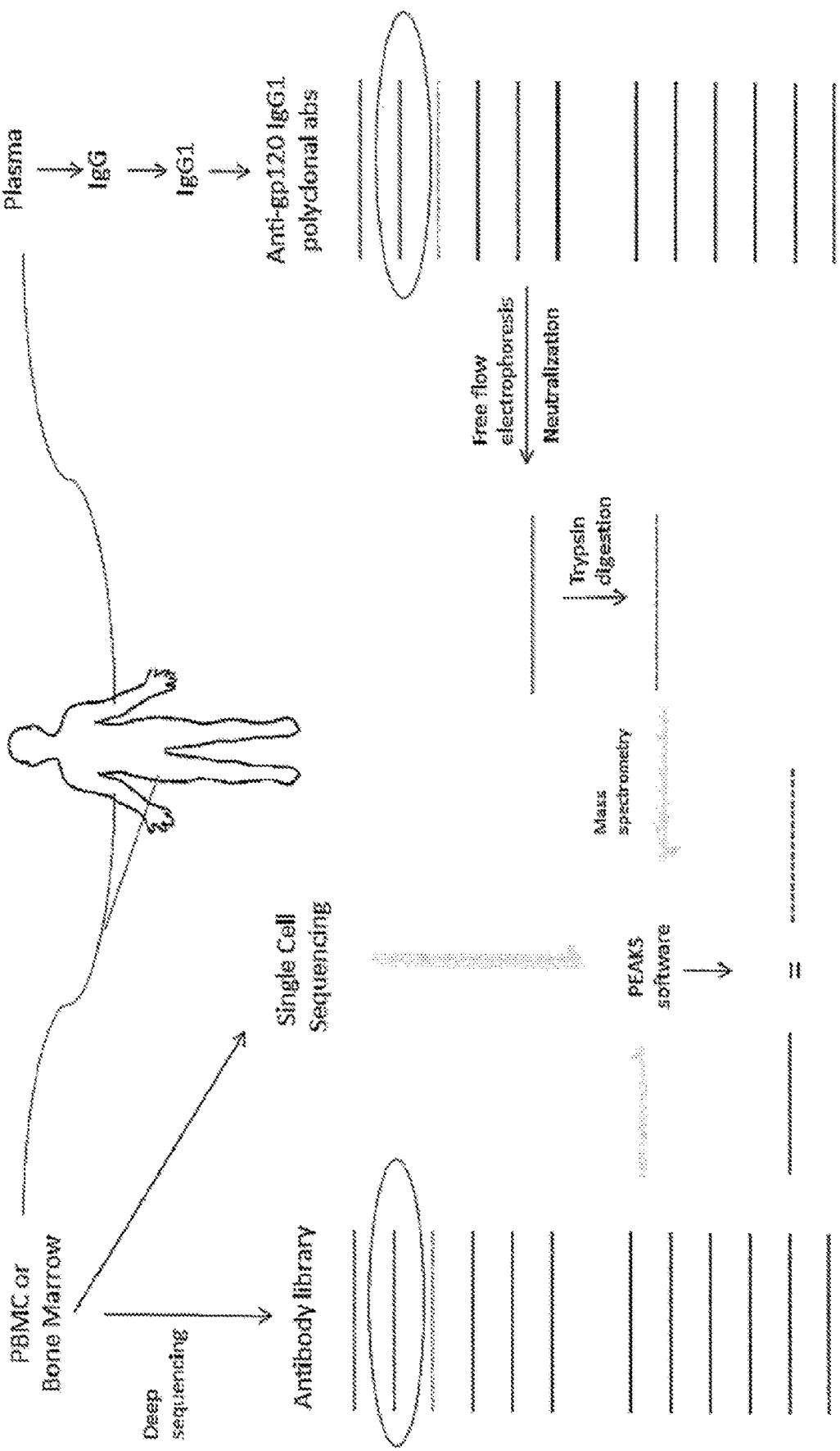
FIG. 3. Targeted sequencing of plasma antibodies. Antibody is isolated to the fraction of interest after affinity purification and FFE. The fraction or region of interest was digested by trypsin (and/or chymotrypsin and Glu-C) and then subjected to LC-MS. A patient specific database of B cells from PBMC and bone marrow was made from deep sequencing and single-cell sequencing. For deep sequencing, we used unsorted PBMCS, bone marrow CD138– cells, and bone marrow CD138+ cells. For single-cell sequencing we used Yu2-gp140 reactive memory B cells, circulating plasmablasts, and CD138-CD38hi bone marrow cells. CD38hi bone marrow was also subjected from a different time point (2.5 years later) with additional sorting on CD138 and CD19 to single-cell sequencing. The peptide sequences were reconciled with the B cell database with Peaks software (Ontario, Calif.). For deep sequencing data, an algorithm (based on somatic hypermutation, percent antibody coverage, number of digests found in, frequency of antibody in the database, CDR3/CDL3 length/deletion) was developed to identify top-scoring antibody sequences. For single-cell sequencing, a different algorithm was used mainly relying on unique peptides to identify top-scoring antibody sequences. Top scoring antibodies were manufactured and screened on gp120 reactivity (for the deep sequencing database) or gp120 reactivity and neutralization (single-cell sequencing). A total of 14 antibodies (at least 10% divergent from each other) and several related clones were isolated.

The neutralizing anti-gp120 immunoglobulin (Ig) fraction with κ light chains (see Methods) recovered from NVS60 plasma represented a minor portion of the total immunoglobulin IgG response (approximately 1% of the total mass). The anti-gp120 κ Ig preparation was then subjected to free flow isoelectric focusing (FFE) to further fractionate antibody species (total 40 fractions) according to pI. Our previous studies determined that the broadly neutralizing antibodies in NVS60 reflected basic pI. Accordingly, FFE fractions were selected for analyses if they corresponded to a pI of 8.5-9. M. M. Sajadi et al., *J Virol* 86, 5014-5025 (2012). These were confirmed with ELISA using an array of gp120 and mutants known to indicate reactivity with specific epitopes and confirmatory neutralization testing, the results of which matched previous know characteristics of fractions of the same pI (FIG. 2). M. M. Sajadi et al., *J Virol* 86, 5014-5025 (2012).

Immunoglobulins (3 ug-50 ug) from the FFE fractions from the regions of interest were subjected to enzymatic digestion (see Methods). In addition, unfractionated affinity purified fractions were also digested. Peptide fragments were then subjected to LC-MS to generate mass assignments and their deduced amino acid sequences (see Methods).

A subject-specific Ig gene database was derived from single-cell sequencing of bone marrow cells (IgA$^-$IgM$^-$IgD$^-$CD19+CD20$^-$CD27$^+$CD38$^{hi}$CD138$^-$) and circulating plasmablasts (IgA$^-$IgM$^-$IgD$^-$CD19$^+$CD20$^-$CD27$^+$CD38$^{hi}$) that yields paired heavy and light chain sequences (see Methods). An array of whole IgG H and L amino acid sequences were translated from the database and used as a basis for interpreting the peptide data. The deduced peptide sequences were assembled and aligned using Ig amino acid sequences translated from the NVS60 genetic database as templates. Such alignments maintained a tolerance threshold consistent with the overall peptide mass. Mass spectroscopy data analysis settings were Parent Mass Error Tolerance 5.0 ppm, Fragment Mass Error Tolerance 0.5 Da, Fixed modification of Carboxymethyl (58.01), and False Discovery Rate for peptides 5% to validate the probability that a serum Ig sequence was correctly identified (see Methods for further details). Potential antibodies were ranked based on number of unique peptides in the heavy and light chain sequences (see Methods for further details). Seventeen sequences from the database with the highest scores (most unique peptides) were used as a template to synthesize H and L Ig chains. The plasma peptides achieved up to 96% coverage for these antibodies, and any peptide gaps were filled from the matched database sequences. The heavy and light chains which were expressed as mAbs and tested by ELISA for binding to the gp120 used for affinity chromatography and for HIV neutralization (Tables 4 and 5).

Of the 17 putative anti-gp120 mAbs, 13 either bound to gp120 on ELISA and/or were able to neutralize one of the 15 Tier1-3 strains tested. The remaining 4 of the 17 mAbs (representing the lower end of the scoring system, and thus less unique peptides) did not bind gp120 or neutralize HIV-1 (Table 4). One additional mAbs (N60P47), related to the Cluster C CD4i mAb N60P39 was discovered after a homology search of the database. This mAb had roughly the same peptide coverage as the others in its lineage, but had no unique peptides and thus was not identified. Interestingly, a homology search of the bone marrow database did not reveal any of the ancestral forms of any of the mAbs identified. In all, we discovered 14 mAbs with anti-HIV reactivity (summarized in Table 5). All of the mAbs were found in the bone marrow, and only one of these (N60P22) was additionally seen in the circulating plasmablast population (Table 5). Importantly, the reconstructed mAbs exhibited both protein specificity and isoelectric points closely matching those of the IEF fractions (FIG. 9).

Figure 4:
FIG. 4. Dendrogram of variable region of all NVS60 antibodies derived from single-cell sequencing from the bone marrow. The antibodies isolated from 2013 grouped into 6 distinct families. Two families of CD4-BS antibodies were identified. The VRC01-like which contained the broad neutralizing antibodies and could not bind YU2 core, and another group which was not broad, which could bind YU2-core. CD4-BS=CD4-binding site antibodies. CD4i=CD4-induced antibodies. V3=Variable loop 3 antibodies.
Figure 5:
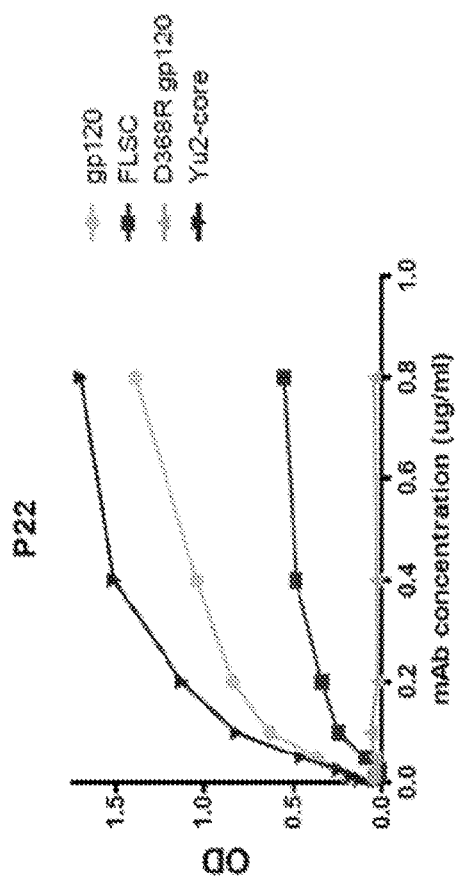
FIG. 5. ELISA Reactivity of the 6 families of antibodies isolate. Representative examples of each family is given. Dilutions of each mAb was tested by ELISA for reactivity against the indicated HIV antigens: BaL-gp120 monomer, BaL-gp120 monomer with the D368R mutation to abrogate CD4-BS binding, Yu2 gp120 core, and full length single chain (FLSC), presenting a full length CD4-induced gp120 structure in which the CD4-BS is occupied. N60P35 was also tested against YU2 gp120 core with the V3 loop. X-axis shows mAb concentration in ug/ml, and Y axis the background-subtracted OD. CD4-BS=CD4-binding site antibody. CoR-BS=Co-Receptor binding site antibody. CD4i=CD4-induced.
Figure 5:
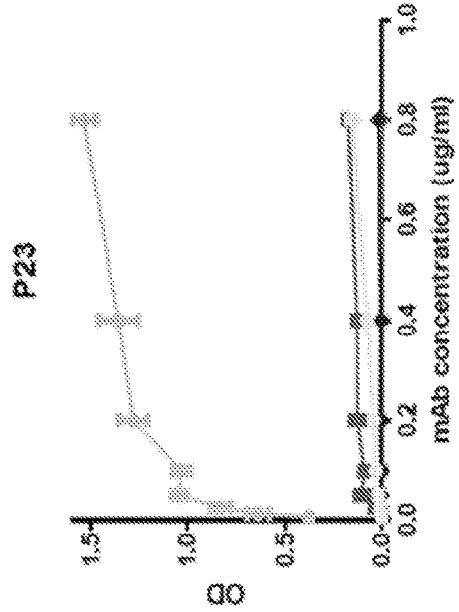
Figure 5:
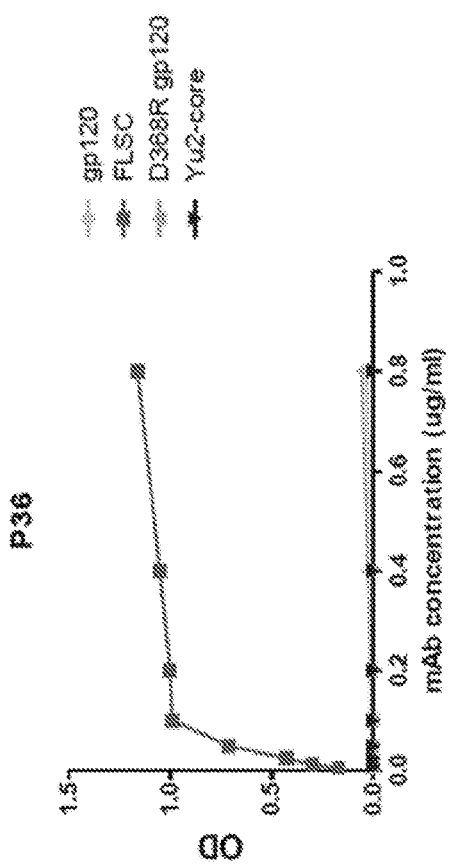
Figure 5:
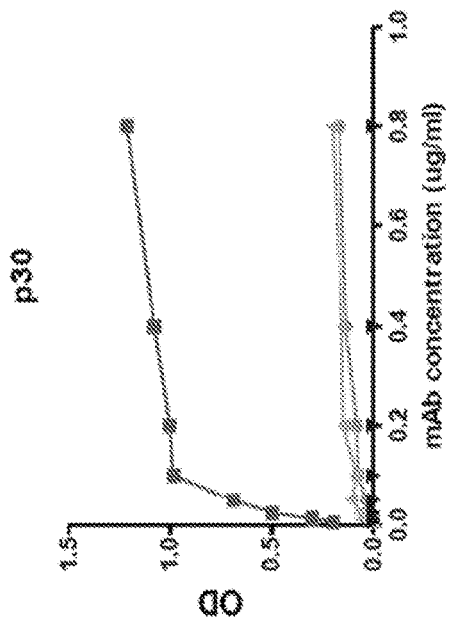
Figure 5:
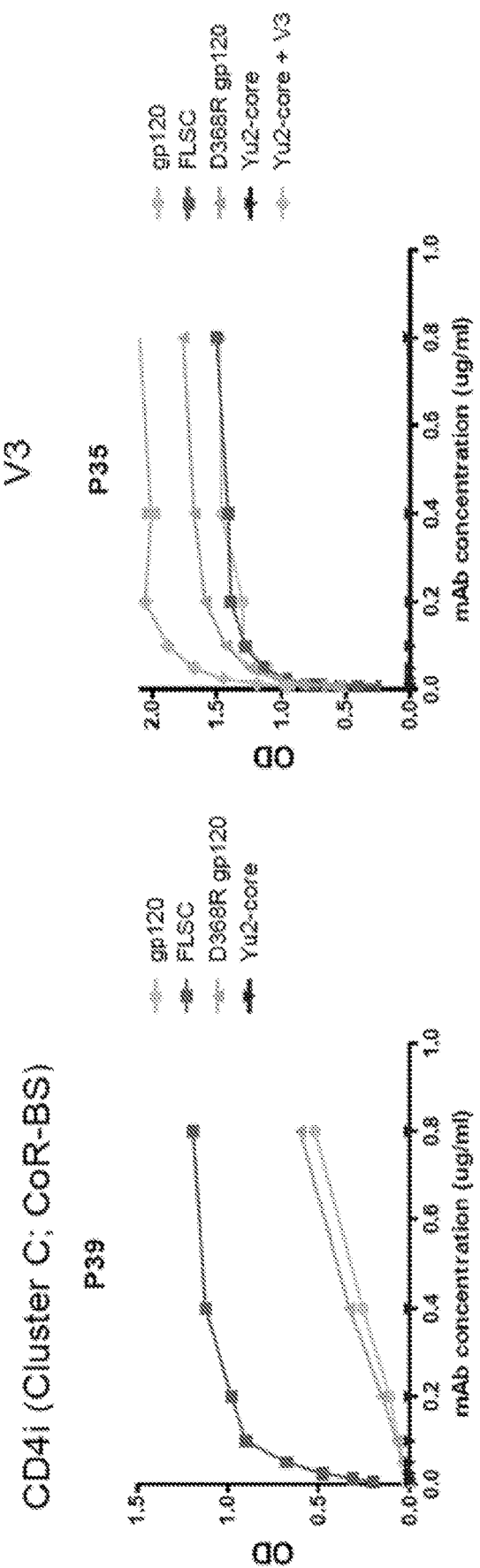
Figure 6:
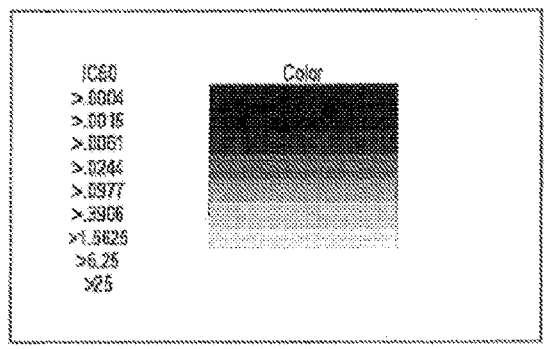
FIG. 6. Heat map showing neutralization activity of N60P23. The log $IC_{50}$ neutralization values on a panel of 120 viral strains (individual viruses listed on the left column). $IC_{50}$ values are color-coded according to the color key on the left: the greater the neutralization, the darker red the color; light white represents no neutralization ($IC_{50}$>25 ug/ml). Sample N60 (polyclonal anti-gp120 ab) shown as comparison. There was a 65% homology between N60P23 and the parent neutralization, and there were no additional viral strains neutralized by N60P23 (not neutralized by the parent fraction). The data suggest antibody cooperativity is needed to reach the full neutralization breadth of the plasma.
Figure 6:
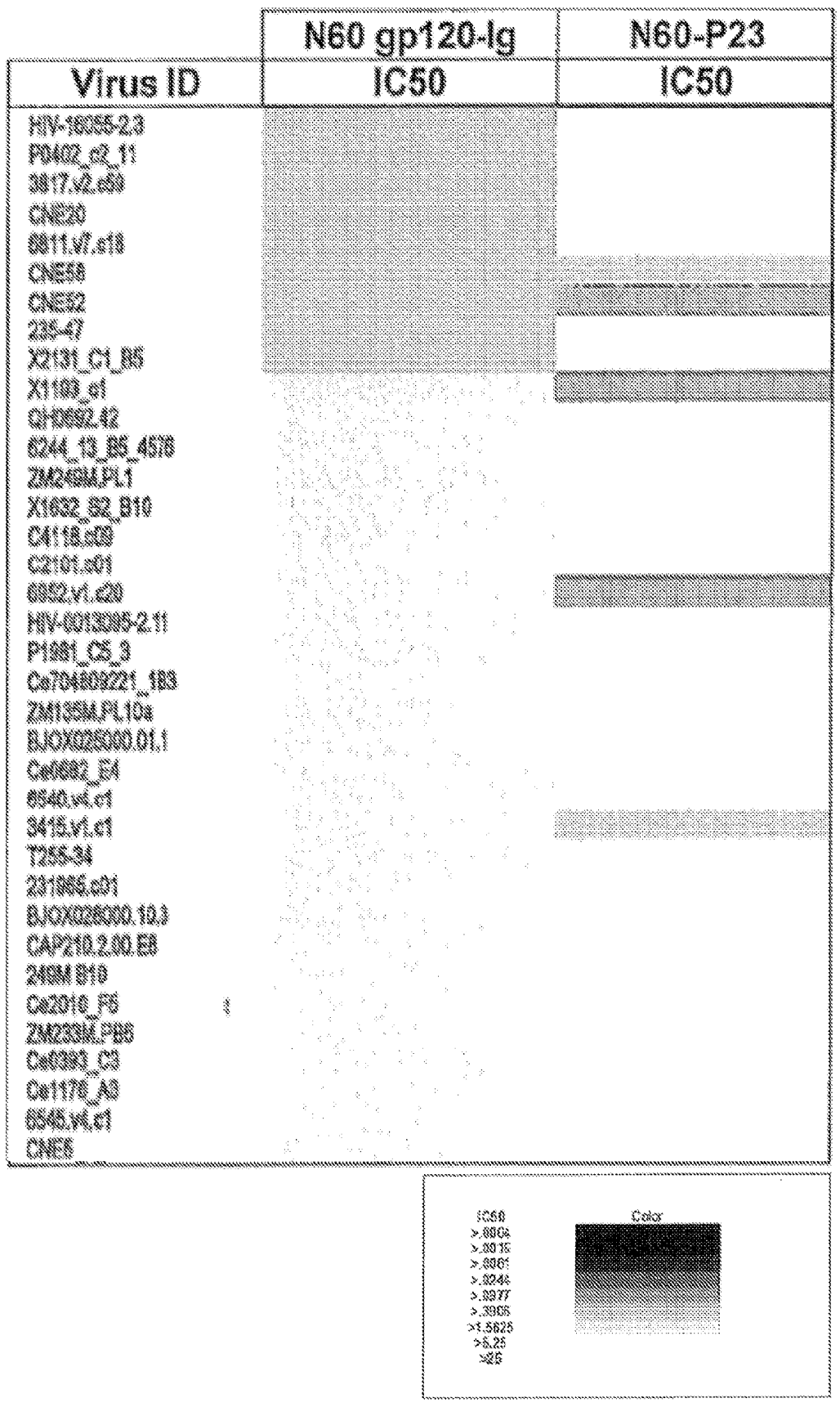
Figure 6:
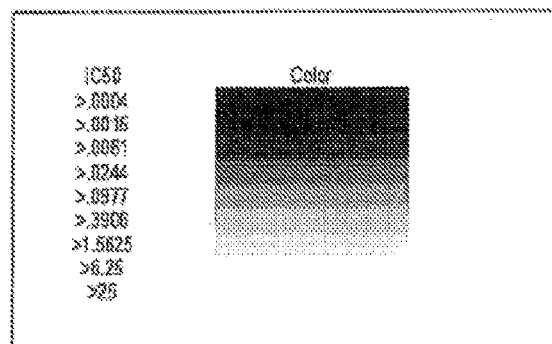
Figure 7B:
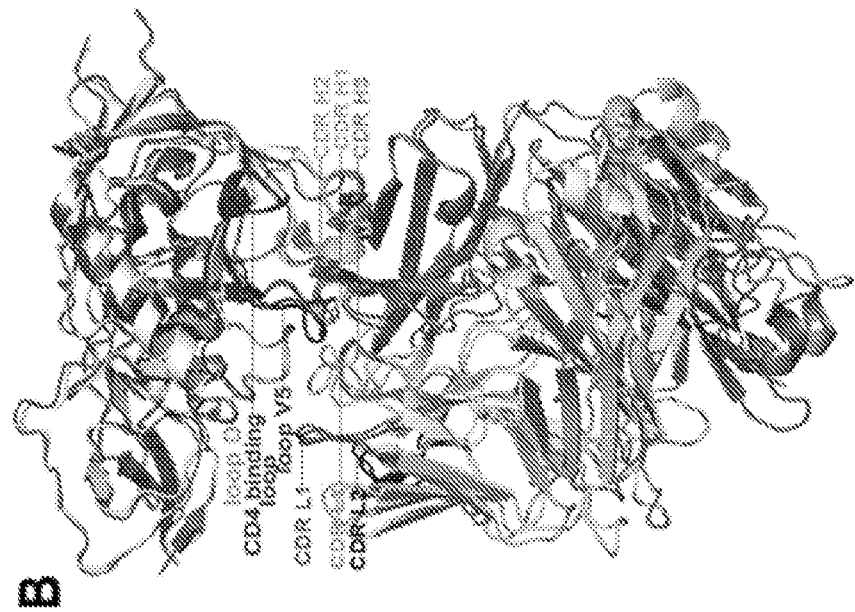
FIG. 7. Crystal structure of N60P23 Fab-gp120$_{93TH057}$ core$_e$ complex. (A) Ribbon diagram of N60P23 Fab-gp120$_{93TH057}$ core$_e$ complex with light and heavy chains of Fab shown in light and dark green, respectively, and the complementarity-determining regions (CDRs) shown in blue (CDR L1), black (CDR L2), orange (CDR L3), pink (CDR H1), green (CDR H2), and yellow (CDR H3). The gp120 is colored in white. The D (S274-T283), V5 (T455-N465) and the CD4 binding (Q362-G372) loops are colored in cyan, violet and magenta, respectively. (B) Structural comparison of N60P23 Fab-gp120$_{93TH057}$ core$_e$ complex and VRC01-gp120$_{93TH057}$ core$_e$ (PDB code 3NGB, complexes. M. Pazgier et al., Proc Natl Acad Sci USA 106, 4665-4670 (2009). Complexes were aligned based on the gp120 and are shown as the ribbon diagrams. The light and heavy chains of VRC01 Fab are shown in light and dark cyan and the CDRs are colored as in N60-p23 complex. (C) N60P23 and VRC01 epitope footprints. N60P23/VRC01 contacts on gp120$_{93TH057}$ core$_e$ are highlighted in light green/cyan (light chain) and dark green/cyan (heavy and both chains) on the gp120 surface. (D) N60P23 and VRC01 Fabs and gp120$_{93TH057}$ core$_e$ contact residues on the primary sequence of the Fabs and gp120$_{93TH057}$ core$_e$, respectively. Residues contributing to the Fabs and gp120$_{93TH057}$ core$_e$ are highlighted and contacts as defined by a 5 Å cutoff are marked above the sequence. Side chain (+) and main chain (−) contacts are colored based on contact type; hydrophobic in blue, hydrophilic in green, or both in black. Framework and complementary-determining regions are as indicated in the alignment.
Figure 7A:
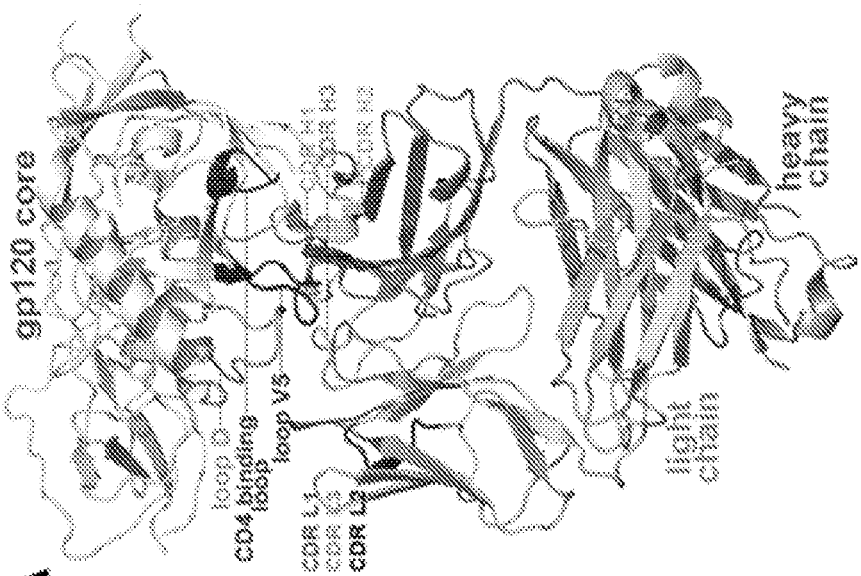
Figure 7C:
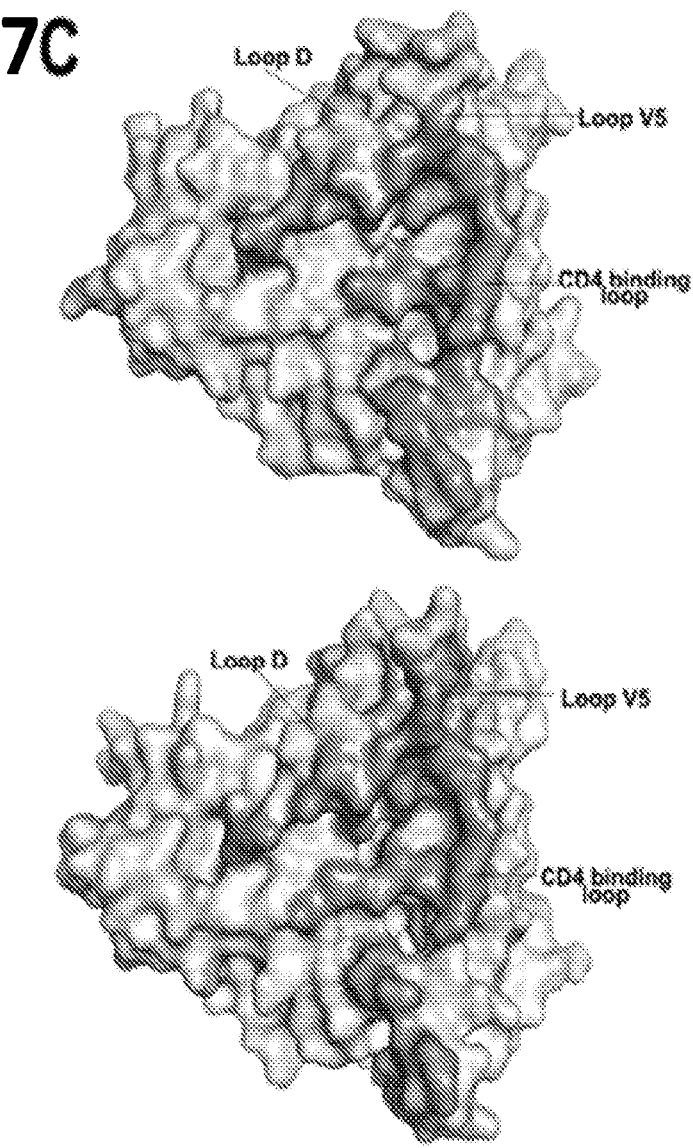
Figure 7D:
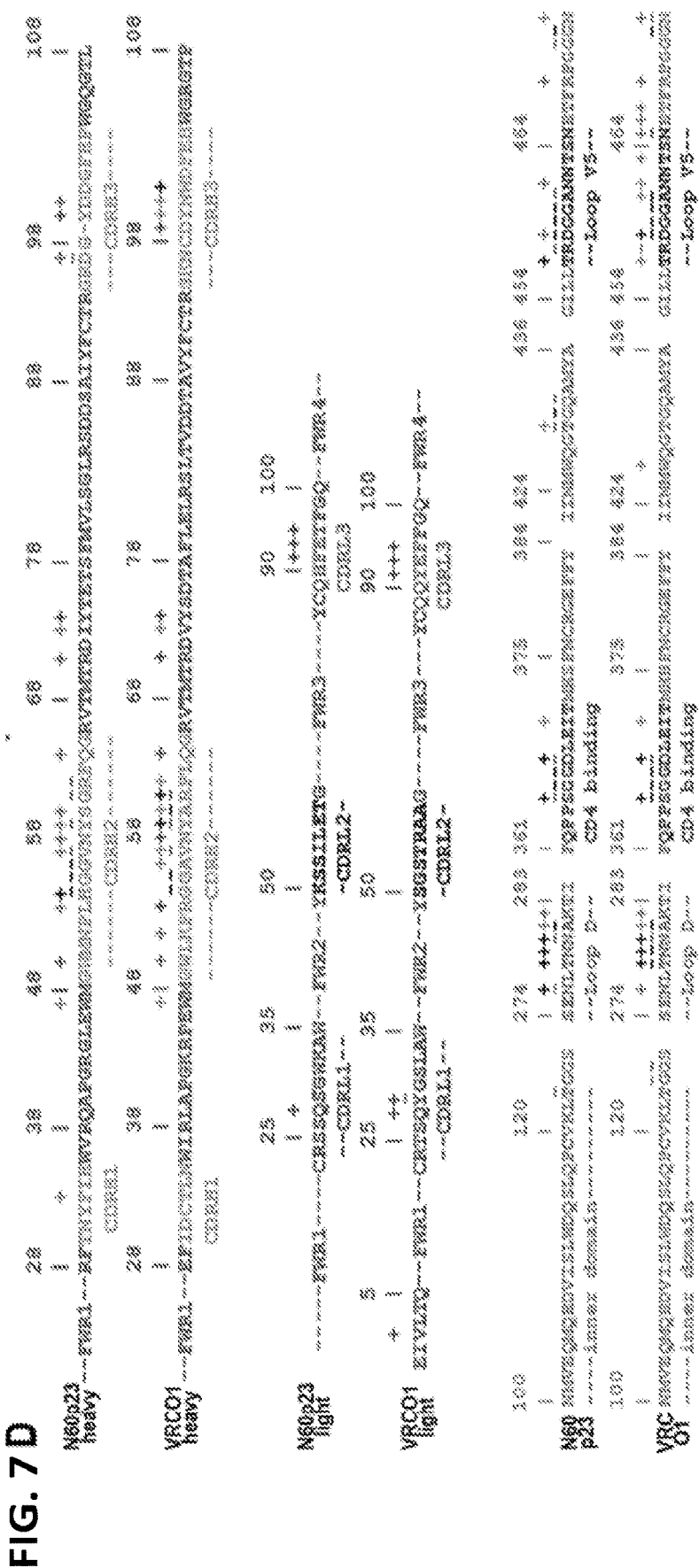

Overall, the dominant plasma anti-gp120 response appeared to comprise 11 distinct antibody species (as defined by <95% heavy chain variable region homology with any other antibody) arising from 6 distinct lineages (FIG. 4). These included 2 separate families of anti-CD4-BS antibodies, 3 families of anti-CD4i antibodies, and one family of anti-V3 antibodies. During the course of a previous study (M. M. Sajadi et al., *J Infect Dis* 213, 156-164 (2016)), we determined that the κ/λ ratio of the anti-gp120 response was 0.52 in this patient. Anti-V3 antibodies were the only specificity we found for this patient in the IgG1λ fraction (FIG. 4). Within this family, we only found one dominant lineage, thus these antibodies could account for up to 60% of the anti-gp120 response. Epitope assignment was primarily based on ELISA (FIGS. 5 and 11). Suspected specificities were confirmed by competition ELISAs with epitope-specific mAbs and/or biacore (Table 5 and data not shown).

Among the 6 anti-gp120 lineages, only one family of mAbs (comprising N60P2.1, N60P23, N60P25.1, N60P31.1) exhibited broad and potent neutralizing activity, matching 90% of the coverage observed with whole plasma anti-gp120 Ig (FIG. 10) The prototypical antibody of this family, N60P23 demonstrated specificity for the CD4-BS (FIG. 2).Two mAbs, N60P23 and N60P25.1, demonstrated particularly strong neutralizing activity (Table 2), matching 70% and 73% of the affinity purified fraction breadth, respectively. Thus, broad plasma neutralizing activity in the subject arises from a minority of the antibody repertoire at the sample time points we evaluated (FIG. 4). All four broadly neutralizing mAbs resembled known VRC01-like anti-CD4-BS antibodies in that they belonged to the 1-2 heavy chain and 1-5 light chain family; exhibited a deletion in the CDRL3. L. D. Williams et al., *Science Immunology* in press, (2017); M. M. Bonsignori et al., *J Immunol* 183, 2708-2717 (2009); G. K. Lewis et al., *Proc Natl Acad Sci USA* 111, 15614-15621 (2014). The identity of the corresponding CD4-BS epitope was further confirmed by crystallographic analyses (FIG. 7). N60P23 Fab was bound to the CD4gp120$_{93TH057}$ core$_e$, and crystal structures revealed a similar foottprint to VRC01 (FIG. 7). We had previously shown that neutralizing antibodies with breadth typically have a basic pI of 8 to 9 and target acidic epitopes. M. M. Sajadi et al., *J Virol* 86, 5014-5025 (2012). In this patient, we were able to confirm this with x-ray crystallography (FIG. 7).

The paratope of N60-p23 in the gp120$_{93TH057}$ core$_e$ complex is predominantly electropositive with basic charges contributed mainly by CDR H1 and H2. There is a good electrostatic complementarity between the antibody combining site of N60P23 and the targeted gp120 surface.

Despite their potency, none of the six mAbs tested individually was able to fully replicate the breadth of the NVS60 plasma neutralizing response. Specifically, ten percent of pseduoviruses, independent of their clade or Tier, were sensitive to affinity purified polyclonal anti-gp120 Ig but were not demonstrably neutralized by any one CD4-BS mAb (Table 2). Notably, one of the disparate pseudoviruses (not able to be neutralized by CD4-BS mAbs) was neutralized by the CD4i mAb N60P39. To determine if breadth could be established by a polyclonal mixture of plasma-derived antibodies, an equimolar pool of all anti-CD4 BS mAbs and an equimolar combination of all anti-CD4-BS, anti-CD4i and anti-V3 mabs (the latter combination re-assembling the identified polyclonal anti-gp120 response) were tested against the virus panel. However, neither pool duplicated the full spectrum of polyclonal neutralizing activity produced by the natural mixture of anti-gp120 antibodies found in plasma (Table 2). Again, the same array of viruses were sensitive to the plasma anti-gp120 IgG but resistant to the mAb pool. These results suggest that full plasma neutralization breadth involves either a cryptic anti-gp120 specificity peculiar to a small subset of virions or a molar ratio of specificities that we could not readily duplicate by simple antibody mixing in vitro.

Anti-gp120 humoral responses are characteristically short-lived in animal models, gp120-vaccinated subjects (such as the RV144 trial) and naturally infected humans. M.

Figure 8:
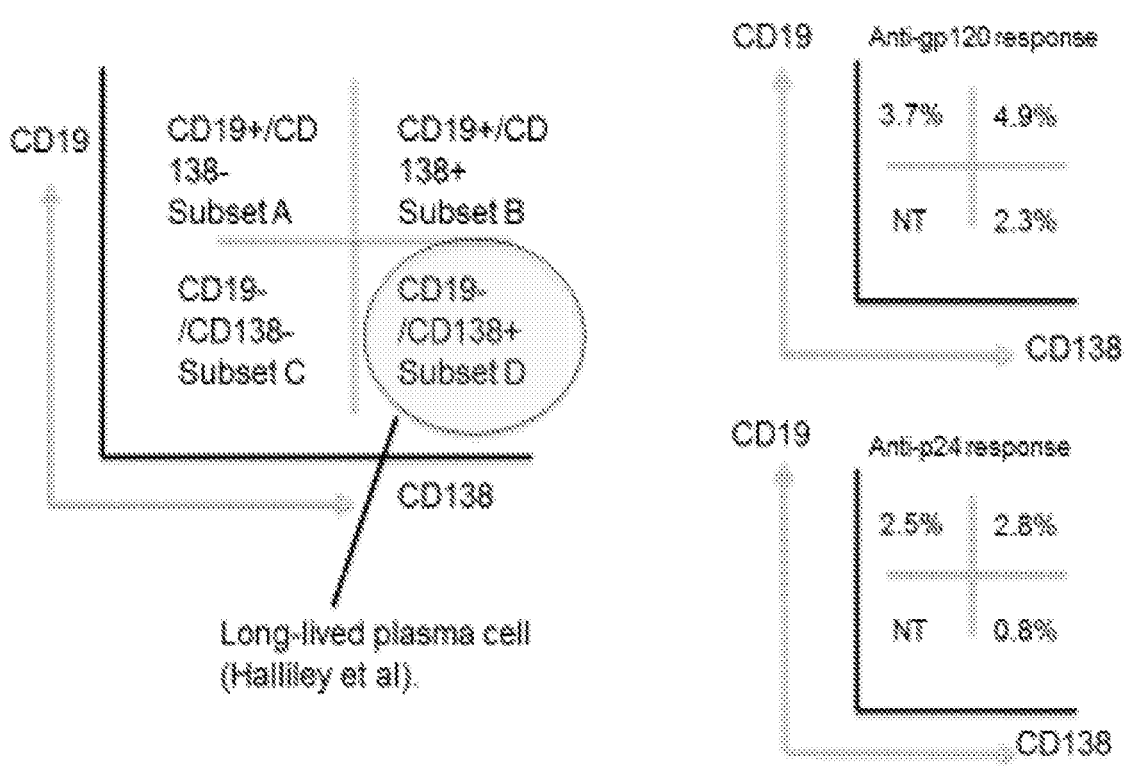
FIG. 8. Frequency of anti-HIV Env antibodies in plasma cell compartments. Following the algorithm recently published by Halliley et al., we sorted the CD38Hi cells based on CD19 and CD138. Halliley et al., Immunity 43, 132-145 (2015). Anti-gp120 antibodies were seen in similar frequencies in each of the compartments tested, similar to the anti-p24 response. Plasma cells secreting anti-gp120 antibodies were also detected in Subset D, which contains the long-lived plasma cells.

M. Bonsignori et al., J Immunol 183, 2708-2717 (2009); G. K. Lewis et al., Proc Natl Acad Sci USA 111, 15614-15621 (2014); B. J. Morris et al., J Exp Med 188, 233-245 (1998); S. Rerks-Ngarm et al., N Engl J Med 361, 2209-2220 (2009). HIV-positive persons placed on ARVs exhibit rapid declines in anti-gp120 titers, and within a year experience 2-3 fold decreases of titers. M. M. Bonsignori et al., J Immunol 183, 2708-2717 (2009); G. K. Lewis et al., Proc Natl Acad Sci USA 111, 15614-15621 (2014); B. J. Morris et al., J Exp Med 188, 233-245 (1998). One possible reason for this characteristic is that long-lived anti-gp120 plasma cells fail to establish a niche in the bone marrow. Accordingly, we examined whether the plasma anti-gp120 antibodies were expressed by bone marrow plasma cells exhibiting the long-lived cell phenotype (CD38hi, CD19–, CD138+ (23)). A new database was constructed for gp120-specific CD19+ CD138+ and CD19– CD138+ bone marrow cells; a parallel database was constructed for p24-specific antibodies (3 antibodies from 2 different clonal lineages) that were identified in contemporaneous NVS60 plasma (data not shown) using an analogous fractionation, sequencing and deconvolution procedure. Anti-gp120 responses are thought to have different regulation that anti-p24 antibody response, so we wanted to analyze this response as well. K. P. Binley et al., J Virol 71, 2799-2809 (1997). We were able to detect anti-gp120 and anti-p24 antibodies at similar frequencies in all of the subsets analyzed, including the long-lived plasma cell subset (FIG. 8). Even though the CD138– population is about 10× higher than the CD138+ population in this patient, the high frequencies of anti-gp120 specificities in the long-lived plasma cell subset suggests that the lack of a persistent HIV gp120 response during natural infection is not due to aberrant establishment of such cells in the bone marrow. Given that there seems to be adequate frequency of anti-gp120 plasma cells, and that we did not find clonal ancestors of the mAbs in any of the subsets, the regulation of the long-lived plasma cells may be responsible for the lack of durable immunity.

Under the rubric that adaptive immunity to HIV infection provides a blueprint for envelope-based vaccine design and antibody-based prevention, we deconvoluted a broadly neutralizing plasma profile that is shared by similar HIV-infected subjects and tracks to epitopes extant on monomeric gp120 (and FIGS. 2 and 5; Table 5). M. M. Sajadi et al., J Virol 86, 5014-5025 (2012); P. Rusert et al., Nat Med, (2016). A number of insights are revealed by this exercise. First, while previous studies have demonstrated that the anti-gp120 response is limited to a number of epitopes, we demonstrate that the overall polyclonal anti-gp120 plasma response is not only limited to a handful of epitopes but antibodies as well. L. M. Walker et al., PLoS Pathog 6, e1001028 (2010); P. Rusert et al., Nat Med, (2016). For example, one antibody family (anti-V3 antibodies) comprising only two members accounted for over 50% of the anti-gp120 antibodies made by this person (thus up to 1% of the total circulating IgG1). In NVS60, six separate events representing the 6 clonal lineages (FIG. 4) dominated the germinal center (and/or non-germinal center) reactions to produce the dominant response. This dominant array differs from what is typically seen in the memory B cell compartment, which reflect a comparatively larger number of epitopes and antibodies and is known to be discordant with the plasma response. J. F. Scheid et al., Nature 458, 636-640 (2009); Y. Guan et al., Proc Natl Acad Sci USA 106, 3952-3957 (2009). In the latter, the plasma anti-gp120 antibodies were found in the NVS60 memory B cell pool alongside antibody species targeting epitopes not found in circulation. We conclude that the latter are absent in plasma, or exist in such minute quantities that they are undetectable even after fractionation. Second, the broad and potent neutralizing antibodies were functional in plasma despite being only a minor fraction of the total circulating polyclonal response (less than 1% of the total IgG). This number is similar to the frequencies found in the bone marrow, which has shown previously shown to correlate with serum titers. J. M. Montezuma-Rusca et al., J Immunol 194, 2561-2568 (2015). It has been argued that "non-neutralizing" anti-gp120 responses prevent broadly neutralizing antibody responses from appearing or acting in circulation. I. S. Georgiev et al., Curr Opin HIV AIDS 8, 382-392 (2013); T. Tong et al., J Virol 86, 3574-3587 (2012); I. S. Georgiev et al., J Virol 89, 5318-5329 (2015); S. W. de Taeye et al., Cell 163, 1702-1715 (2015); R. W. Sanders et al., PLoS Pathog 9, e1003618 (2013). However, the same antibodies mediated broadly neutralizing activity in NVS60 plasma over the course of 5 years (Table 2). Whether the generation of broadly neutralizing antibodies is impeded by non-neutralizing specificities may remain unclear. Nevertheless, the NVS60 response shows that once broadly neutralizing antibodies arise in circulation they are not necessarily erased by contemporaneous non-neutralizing antibody responses. Third, CD4-BS antibodies are responsible for nearly all of the broad and potent neutralization breadth seen in this patient's plasma. These antibodies shared a number of key structural motifs (including the deletion in CDRL3, inability to bind the D368R mutant, almost identical epitope footprint with crystallography) with VRC01-like anti-CD4-BS derived from the memory B cell population of a separate subject.

In summary, these analyses show how very broadly neutralizing anti-gp120 plasma responses in a single person can be pauciclonal, comprising related antibodies with matching epitopes; that individual neutralizing antibodies function and persist within a much larger plasma milieu of non-neutralizing or poorly neutralizing antibodies; that the neutralizing antibodies are expressed by long-lived plasma cells; and that the neutralizing antibodies detected in the B cells of a variety of HIV-infected persons share common structural properties and specificities presented by a relatively a relatively straightforward monomeric gp120 structure. Collectively, these features offer encouraging support for practical efforts to generate broadly neutralizing responses via vaccination with gp120-based immunogens. Indeed, analyses such as reported here help provide a framework for determining the degree to which vaccination resembles natural adaptive immunity to HIV infection where neutralizing antibodies arise. Of course, the virological and immunological conditions that launch broadly neutralizing responses remain undecided. These conditions might be elucidated by longitudinal deconvolution of plasma responses from the time of acute infection, using methods such as those described here.

TABLE 1

Neutralization of N60 parent and affinity purified samples. Pro A/G = plasma sample that has been run over a Protein A/G column to isolate IgG1-4 gp120 = Pro A/G sample that has been run over a BaL-gp120 (monomer column). gp120-IgG1 = Pro A/G sample that has been run over a BaL-gp120 (monomer column) and then an IgG1 column. IC50 = Inhibitory concentration 50 (ug/ml). T/F = transmitted/founder Plasma from patient NVS60 was purified and tested against a 120 pseudovirus panel. Parent sample demonstrates considerable breadth, which was also seen in the gp120 and gp120-IgG1 fractions.

| | | Titer in TZM.bl cells (ug/ml) | | |
|---|---|---|---|---|
| Virus ID | Clade* | NV60 Pro A/G IC50 | NVS60 gp120 IC50 | NVS60 gp120-IgG1 IC50 |
| 6535.3 | B | 23.629 | 2.337 | 1.399 |
| QH0692.42 | B | 73.193 | 10.496 | 5.384 |
| SC422661.8 | B | 30.877 | 3.333 | 2.194 |
| PVO.4 | B | 23.164 | 1.478 | 1.005 |
| TRO.11 | B | 35.183 | 7.264 | 5.693 |
| AC10.0.29 | B | 27.920 | 4.144 | 3.550 |
| RHPA4259.7 | B | 14.971 | 3.373 | 2.257 |
| THRO4156.18 | B | 42.864 | 17.930 | 6.848 |
| REJO4541.67 | B | 21.061 | 4.071 | 3.186 |
| TRJO4551.58 | B | 72.808 | 16.072 | 13.344 |
| WITCO4160.33 | B | 151.278 | 46.052 | 23.311 |
| CAAN5342.A2 | B | 30.870 | 4.007 | 3.148 |
| WEAU_d15_410_787 | B (T/F) | 32.622 | 4.254 | 2.479 |
| 1006_11_C3_1601 | B (T/F) | 31.461 | 5.019 | 3.047 |
| 1054_07_TC4_1499 | B (T/F) | 104.772 | 27.878 | 10.870 |
| 1056_10_TA11_1826 | B (T/F) | 209.754 | 22.420 | 12.264 |
| 1012_11_TC21_3257 | B (T/F) | 39.521 | 3.783 | 2.738 |
| 6240_08_TA5_4622 | B (T/F) | 216.472 | 45.439 | 38.068 |
| 6244_13_B5_4576 | B (T/F) | 58.906 | 4.678 | 4.487 |
| 62357_14_D3_4589 | B (T/F) | 60.360 | 11.454 | 8.697 |
| SC05_8C11_2344 | B (T/F) | 28.437 | 4.712 | 3.912 |
| Du156.12 | C | 37.524 | 6.824 | 5.405 |
| Du172.17 | C | 119.944 | >50 | 38.171 |
| Du422.1 | C | 46.145 | 17.533 | 14.580 |
| ZM197M.PB7 | C | 28.614 | 14.055 | 4.300 |
| ZM214M.PL15 | C | 485.829 | >50 | >50 |
| ZM233M.PB6 | C | 169.452 | 21.342 | 20.248 |
| ZM249M.PL1 | C | 102.326 | 15.919 | 12.597 |
| ZM53M.PB12 | C | 25.867 | 10.571 | 6.323 |
| ZM109F.PB4 | C | 210.029 | >50 | 30.049 |
| ZM135M.PL10a | C | 260.838 | 32.686 | 21.300 |
| CAP45.2.00.G3 | C | 350.560 | >50 | >50 |
| CAP210.2.00.E8 | C | 367.728 | >50 | >50 |
| HIV-001428-2.42 | C | 25.972 | 2.701 | 2.187 |
| HIV-0013095-2.11 | C | 211.157 | 22.522 | 18.247 |
| HIV-16055-2.3 | C | 92.761 | 12.576 | 10.268 |
| HIV-16845-2.22 | C | 426.772 | >50 | 49.375 |
| Ce1086_B2 | C (T/F) | 11.192 | >50 | 1.641 |
| Ce0393_C3 | C (T/F) | 142.594 | 30.286 | 15.431 |
| Ce1176_A3 | C (T/F) | 192.528 | 45.344 | 28.479 |
| Ce2010_F5 | C (T/F) | 70.275 | 19.463 | 12.692 |
| Ce0682_E4 | C (T/F) | 64.759 | 17.431 | 10.243 |
| Ce1172_H1 | C (T/F) | >528 | >50 | >50 |
| Ce2060_G9 | C (T/F) | >528 | >50 | >50 |
| Ce703010054_2A2 | C (T/F) | 188.873 | 31.683 | 19.604 |
| BF1266.431a | C (T/F) | 154.369 | 46.996 | 27.310 |
| 246F C1G | C (T/F) | 352.889 | >50 | 48.226 |
| 249M B10 | C (T/F) | 183.182 | 21.542 | 19.517 |
| ZM247v1(Rev-) | C (T/F) | 190.864 | >50 | >50 |
| 7030102001E5(Rev-) | C (T/F) | 33.817 | 3.270 | 3.724 |
| 1394C9G1(Rev-) | C (T/F) | 59.578 | 16.555 | 5.566 |
| Ce704809221_1B3 | C (T/F) | 65.767 | 35.580 | 10.697 |
| CNE19 | BC | 16.594 | 2.854 | 1.520 |
| CNE20 | BC | 15.633 | 4.173 | 1.565 |
| CNE21 | BC | 91.501 | 22.960 | 14.653 |
| CNE17 | BC | 139.056 | 21.438 | 13.846 |
| CNE30 | BC | 221.349 | >50 | 40.694 |
| CNE52 | BC | 56.900 | 7.694 | 5.036 |
| CNE53 | BC | 20.570 | 3.483 | 2.635 |
| CNE58 | BC | 22.749 | 4.549 | 2.858 |
| MS208.A1 | A | 211.293 | >50 | 32.229 |
| Q23.17 | A | 17.575 | 2.938 | 1.794 |
| Q461.e2 | A | >528 | >50 | >50 |
| Q769.d22 | A | 35.201 | 6.293 | 3.506 |
| Q259.d2.17 | A | 33.807 | 7.060 | 3.559 |
| Q842.d12 | A | 18.917 | 3.348 | 2.180 |
| 0260.v5.c36 | A | 80.819 | 13.873 | 43.483 |
| 3415.v1.c1 | A | 46.266 | 4.830 | 4.596 |
| 3365.v2.c2 | A | 54.620 | 8.493 | 5.802 |
| 191955_A11 | A (T/F) | 288.049 | 41.777 | 43.183 |
| 191084 B7-19 | A (T/F) | 34.834 | 4.607 | 1.917 |
| 9004SS_A3_4 | A (T/F) | 18.058 | 2.144 | 1.965 |
| T257-31 | CRF02_AG | 426.998 | >50 | 43.480 |
| 928-28 | CRF02_AG | >528 | >50 | >50 |
| 263-8 | CRF02_AG | 22.824 | 4.205 | 4.064 |
| T250-4 | CRF02_AG | 11.419 | 1.359 | 0.767 |
| T251-18 | CRF02_AG | 371.838 | >50 | 38.744 |
| T278-50 | CRF02_AG | >528 | >50 | >50 |
| T255-34 | CRF02_AG | 131.913 | 15.603 | 12.016 |
| 211-9 | CRF02_AG | 291.355 | 42.611 | 24.418 |
| 235-47 | CRF02_AG | 87.864 | 9.609 | 6.028 |
| 620345.c01 | CRF01_AE | >528 | >50 | >50 |
| CNE8 | CRF01_AE | 194.556 | 16.923 | 7.854 |
| C1080.c03 | CRF01_AE | 483.323 | >50 | >50 |
| R2184.c04 | CRF01_AE | 27.037 | 3.087 | 2.138 |
| R1166.c01 | CRF01_AE | 130.381 | 29.864 | 24.622 |
| R3265.c06 | CRF01_AE | 440.886 | >50 | >50 |
| C2101.c01 | CRF01_AE | 92.755 | 14.543 | 16.106 |
| C3347.c11 | CRF01_AE | 10.921 | 1.730 | 1.808 |
| C4118.c09 | CRF01_AE | 117.159 | 17.416 | 16.615 |
| CNE5 | CRF01_AE | 170.243 | 20.320 | 17.746 |
| BJOX009000.02.4 | CRF01_AE | >528 | >50 | 44.993 |
| BJOX015000.11.5 | CRF01_AE (T/F) | 250.047 | >50 | 26.892 |
| BJOX010000.06.2 | CRF01_AE (T/F) | >528 | >50 | >50 |
| BJOX025000.01.1 | CRF01_AE (T/F) | 328.505 | >50 | >50 |
| BJOX028000.10.3 | CRF01_AE (T/F) | >528 | >50 | >50 |

TABLE 2

Plasma neutralization potency and breadth from 2008-2013. Plasma from patient NVS60 was tested against a panel of multiclade HIV pseudoviruses. Numerical values given as ID50, the Inhibitory Dose 50.

| | | Plasma ID50 Titer in TZM.bl Cells (1/x) | | | |
|---|---|---|---|---|---|
| Virus | Clade | Oct. 1, 2008 | Oct. 12, 2009 | Sep. 9, 2010 | Jan. 10, 2013 |
| 6535.3 | B | 3,514 | 2,028 | 2,178 | 1,713 |
| QH0692.42 | B | 530 | 422 | 545 | 335 |
| SC422661.8 | B | 973 | 630 | 650 | 1,008 |
| PVO.4 | B | 1,384 | 548 | 800 | 2,046 |
| TRO.11 | B | 1,820 | 1,074 | 820 | 1,174 |
| AC10.0.29 | B | 3,655 | 1,884 | 1,709 | 1,586 |
| RHPA4259.7 | B | 1,988 | 1,543 | 3,259 | 2,089 |
| THRO4156.18 | B | 1,149 | 721 | 438 | 506 |
| REJO4541.67 | B | 2,112 | 1,576 | 1,133 | 2,143 |
| TRJO4551.58 | B | 269 | 479 | 395 | 728 |
| WITO4160.33 | B | 268 | 221 | 127 | 732 |
| CAAN5342.A2 | B | 6,032 | 2,197 | 1,367 | 1,906 |
| Du156.12 | C | NT | 1,000 | NT | 1,343 |
| Du172.17 | C | NT | 97 | NT | 468 |
| Du422.1 | C | NT | 636 | NT | 581 |
| ZM53M.PB12 | C | NT | 3,183 | NT | 1,715 |
| ZM135M.PL10a | C | NT | 221 | NT | 425 |
| ZM197M.PB7 | C | NT | 455 | NT | 1,062 |
| ZM214M.PL15 | C | NT | 412 | NT | 338 |
| Q23.17 | A | NT | 3,592 | NT | 2,895 |
| Q259.d2.17 | A | NT | 2,873 | NT | 1,528 |
| Q461.e2 | A | NT | 77 | NT | 184 |
| Q168.a2 | A | NT | 1,303 | NT | 942 |
| 3415.v1.c1 | A | NT | 1,097 | NT | 1,318 |
| 0439.v5.c1 | A | NT | 499 | NT | 588 |
| 0260.v5.c1 | A | NT | 3,519 | NT | 1,957 |
| 3365.v2.c20 | A | NT | 869 | NT | 1,425 |
| T257-31 | CRF02_AG | NT | 97 | NT | 316 |
| 263-8 | CRF02_AG | NT | 493 | NT | 1,104 |
| T211-9 | CRF02_AG | NT | 108 | NT | 780 |
| MuLV (Neg) | Control | 24 | 30 | <20 | 186 |

NT = not tested.

TABLE 3

IC50 and ED50 of N60 Plasma and gp120-FT. Plasma from patient NVS60 as well as gp120-FT (IgG that was passed over a BaL-gp120 column) was tested against a panel of HIV pseudoviruses for neutralization as well as Bal.26 for binding. Numerical values given as dilutions of the Inhibitory Dose 50 (ID50) or the Effective Dose 50 (ED50). In each case, the gp120-FT loses potency (partially or completely) compared to the parent plasma.

| Virus | Clade | plasma | gp120 FT |
|---|---|---|---|
| BaL.26 | ED50 | 46,728 | 1,137 |
| BaL.26 | ID50 | 3,065 | 152 |
| REJO4541.67 | ID50 | 79 | <30 |
| TRJO4551.58 | ID50 | 82 | 50 |
| VSV (Neg) | ID50 | <30 | <30 |

TABLE 4 mAb screening ELISA and neutralization. For BaL-gp120 ELISA binding, background subtracted OD results shown for mAbs tested at 8 ug/ml. For HIV-1 neutralization, a neutralization was carried out against a panel of Tier 1-3 pseudoviruses (see Methods). The lowest reported IC50 value of all pseudoviruses tested is reported above. 14/18 antibodies that were targeted bound or neutralized HIV.

| | ELISA binding (OD) | HIV neutralization (IC50) |
|---|---|---|
| N60P2.1 | 0.196 | 1.683 |
| N60P22 | 1.392 | 1.275 |
| N60P23 | 1.535 | 0.44 |
| N60P25.1 | <0.05 | .246 |
| N60P27 | <0.05 | >50 |
| N60P30 | 0.169 | >50 |
| N60P31.1 | <0.05 | 1.807 |
| N60P35 | 1.475 | 0.143 |
| N60P36 | <0.05 | 5.765 |
| N60P37 | 1.42 | 0.6 |
| N60P38 | 1.453 | 5.491 |
| N60P39 | 0.376 | 3.189 |
| N60P39.1 | <0.05 | 0.482 |
| N60P40 | <0.05 | >50 |
| N60P41 | <0.05 | >50 |
| N60P47 | <0.05 | 0.684 |
| N60P48 | .08 | 0.395 |
| N60P52 | <0.05 | >50 |

TABLE 5

Characteristics of anti-gp120 plasma antibodies isolated.

| mAb (2013) | Epitope | PI | Heavy Chain | Light chain | SHM (Heavy/Light) | Peripheral plasmablast | Frequency of CDR3 (per 1000) Single Cell Sequencing | |
|---|---|---|---|---|---|---|---|---|
| | | | | | | | Bone marrow 138− | Bone marrow 138+ |
| N60P2.1 | CD4-BS (VRC01-like) | 8.67 | 1-2 | K 1-5 | 38%/29% | 0 | 2.48 | 0 |
| N60P23 | CD4-BS (VRC01-like) | 8.86 | 1-2 | K 1-5 | 36%/26% | 0 | 2.48 | 1.62 |
| N60P25.1 | CD4-BS (VRC01-like) | 8.94 | 1-2 | K 1-5 | 33%/26% | 0 | 2.48 | 0 |
| N60P31.1 | CD4-BS (VRC01-like) | 8.94 | 1-2 | K 1-5 | 42%/35% | 0 | 2.48 | 0 |
| N60P22 | CD4-BS (Yu2-core binding) | 8.84 | 4-31 | K 3-20 | 9%/11% | 1.62 | 2.48 | 9.69 |
| N60P38 | CD4-BS (Yu2-core binding) | NT | 4-31 | K 3-20 | 9%/11% | 0 | 2.48 | 0 |
| N60P30 | CD4i (Cluster A) | 8.4 | 1-2 | K 3-20 | 21%/12% | 0 | 2.48 | 0 |
| N60P36 | CoR-BS (Cluster C) | 7.57 | 1-69 | K 3-20 | 11%/9% | 0 | 4.96 | 4.85 |
| N60P39 | CoR-BS (Cluster C) | 7.22 | 1-69 | K 3-20 | 11%/9% | 0 | 2.48 | 1.62 |
| N6039.1 | CoR-BS (Cluster C) | 7.5 | 1-69 | K 3-20 | 11%/9% | 0 | 2.48 | 1.62 |
| N60P47 | CoR-BS (Cluster C) | 7.8 | 1-69 | K 3-20 | 16%/6% | 0 | 2.48 | 0 |
| N60P48 | CoR-BS (Cluster C) | 7.2 | 1-69 | K 3-20 | 15%/6% | 0 | 4.96 | 6.46 |
| N60P35 | V3 | 6.92 | 5-51 | L 6-57 | 18%/14% | 0 | 2.48 | 4.85 |
| N60P37 | V3 | 6.92 | 5-51 | L 6-57 | 17%/16% | 0 | 2.48 | 6.46 | mAb = monoclonal antibody.
SHM = somatic hypermutation.
CD4-BS = CD4-binding site antibody.
CoR-BS = Co-Receptor binding site antibody.
Cluster A = competes with A32.
Cluster C = competes with 19e and/or 17b.

Materials and Methods

Patients. The patient identified for this study was selected from the NVS cohort. M. M. Sajadi et al., *J Acquir Immune Defic Syndr* 57, 9-15 (2011); M. M. Sajadi et al., *J Acquir Immune Defic Syndr* 50, 403-408 (2009); M. M. Sajadi et al., *AIDS* 21, 517-519 (2007). NVS patients are defined as having HIV-1 by Western Blot while having an HIV-1 RNA <400 copies/ml for at least 4 measurements and 2 years. This patient's serum was identified as having broad neutralizing activity based on Tier 2 activity and a cross-clade neutralization panel.

Proteins and Antigens. Recombinant HIV-1 antigens were generated as described previously. R. W. Sanders et al., *PLoS Pathog* 9, e1003618 (2013). Test antigens included the YU2 gp120 core, from which V1, V2, and V3 have been deleted; the YU2 gp120 core containing the V3 loop (YU2 gp120 core+V3); monomeric HIV-1 Ba-L gp120; a single chain gp120-CD4 complex (FLSC) presenting a full length CD4-induced Ba-Lgp120 structure in which the CD4 binding site is occupied; and a stabilized, cleaved HIV-1 Ba-L SOSIP trimer (herein designated gp140). L. Wu et al., Nature 384, 179-183 (1996); T. R. Fouts et al., *J Virol* 74, 111427-111436 (2000); A. K. Dey et al., *Virology* 360, 199-208 (2007). An affinity-purified goat Ab (D7324) specific for the C-terminal peptide of HIV-1 gp120 was purchased from Cliniqa (San Marcos, Calif.). All proteins were expressed by transient transfection of 293T cells as previously describe and purified by lectin affinity chromatography as previously described and dialyzed against PBS prior to use. T. R. Fouts et al., *J Virol* 74, 111427-111436 (2000). For crystallographic studies, the gp120 $core_e$ of Clade A/E strain 93TH057 (lacking N-, C-termini, variable loops 1, 2 & 3) was prepared and purified as previously described. P. Acharya et al., *J Virol* 88, 12895-12906 (2014). Deglycosylated gp120$_{93TH057}$ $core_e$ was mixed with a 20% molar excess of N60-p23 Fab and purified by size exclusion chromatography using the Superdex 200 16/60 column (GE Healthcare, Piscataway, N.J.) equilibrated with 25 mM Tris-HCl buffer pH 7.2 with 0.15 M NaCl. The purified complex was concentrated to ~10 mg/ml for crystallization experiments.

Isolation of plasma antibody species. Whole plasma IgG was purified on a Protein A affinity chromatography column (GE Healthcare, Piscataway, N.J.) according to the manufacturer's instructions and dialyzed against PBS prior to use. Affinity chromatography columns were made with activated CH Sepharose beads (GE Healthcare, Piscataway, N.J.) coupled to 2 mg of recombinant HIV-1 Ba-L gp120, as described previously. T. R. Fouts et al., *J Virol* 74, 111427-111436 (2000); Y. Guan et al., *Proc Natl Acad Sci USA* 106, 3952-3957 (2009). Beads specific for human IgG1, human κ chain, and human λ chain were purchased from Capture Select (Naarden, Netherlands). The columns were used to purify antigen-specific IgG (anti-gp120), fractionate IgG1 from whole IgG, or fractionate IgG into κ and λ fractions, as previously described. M. M. Sajadi et al., *J Acquir*

*Immune Defic Syndr* 57, 9-15 (2011); Y. Guan et al., *Proc Natl Acad Sci USA* 106, 3952-3957 (2009). Briefly, IgG was incubated with beads at 37° C. for one hour prior to extensive washing with PBS. Columns were eluted at room temperature with pH 2.8 0.2M glycine (for elution of κ antibodies pH 2.0 was used) and dialyzed against 4 liters PBS 3 times (a minimum of 24 hours total) prior to testing. Dedicated columns were used for each subject and antigen. IgG concentration was measured using an in-house quantitative ELISA as previously described. Y. Guan et al., *Proc Natl Acad Sci USA* 106, 3952-3957 (2009). After a series of steps, the plasma was fractionated into IgG1 κ and IgG1λ antibodies (plasma->protein A column->IgG1 column->kappa and lambda columns), anti-gp120 κ and anti-gp120λ antibodies (plasma->protein A column->gp120 column->kappa and lambda columns), or anti-gp120 antibodies (plasma->protein A column->gp120 column).

Figure 1:
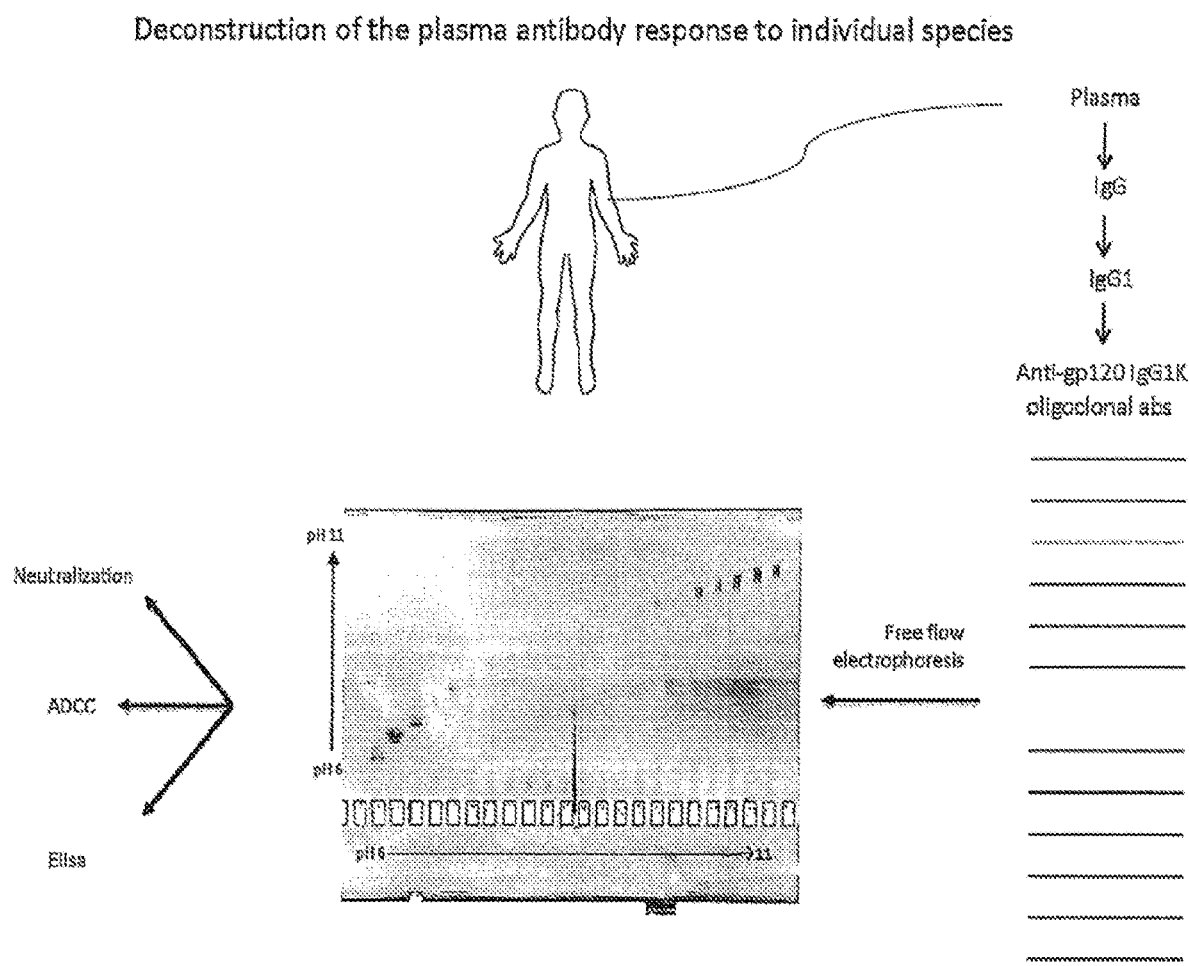
FIG. 1. Deconstruction of the plasma antibody response to individual species. A series of affinity purification isolation steps, the antibodies containing the broad neutralizing activity are separated from plasma (anti-gp120 IgG1 kappa antibodies). These antibodies are subjected to isoelectric focusing to separate the remaining antibodies based on charge (1gG antibodies typically have a PI of 6-10). The individual fractions (up to 50 by Free Flow Electrophoresis) are then run on an pH 6-11 IEF gel to confirm separation. On the gel shown, every other fraction was tested, the gel only as all the fractions cannot all fit on the gel. The antibodies show good separation with only a few bands seen in every fraction. The fractions can then be tested for binding and function to identify the fractions of interest.

Affinity purified and fractioned antibody was subjected to free flow electrophoresis on the BD Free Flow Electrophoresis System (BD,Franklin Lakes, N.J.). The separation, stabilization and counter flow media was freshly prepared according to instructions of manufacturer. The separation and counter flow media contained 0.2% hydroxypropyl methylcellulose (HPMC). The pH range of separation media was 0.88 to 12.8. The media flow rate in the separation chamber was 41 mL/hour. The antibodies (200 to 350 μg/ml) were introduced to separation chamber at the rate of 560 μl/h in the electrical field of 2300V/10 mA/24 W. IEF fractionated samples collected in a 96 deep-well polystyrene microtiter plate, with each well containing 1-2 ml. Approximately half of these wells contained antibody fractionated based on PI. Fractionation was confirmed with pH reading of individual fractions as well as an IEF gel (FIG. 1).

Neutralization assay. HIV-1 neutralization testing was performed using a luciferase-based assay in TZM.b1 cells as previously described. M. M. Sajadi et al., *J Acquir Immune Defic Syndr* 57, 9-15 (2011); M. Li et al., *J Virol* 79, 10108-10125 (2005). This assay measures the reduction in luciferase expression following a single round of virus infection. Stocks of Env-pseudotyped viruses were prepared by transfection of 293T/17 cells as previously described. M. Li et al., *J Virol* 79, 10108-10125 (2005). Fractionated IgG affinity purified samples (anti-gp120 κ) and mAbs were tested against MuLV control and a panel of psuedoviruses. Three-fold serial dilutions of IgG were tested in duplicate (96-well flat bottom plate) in 10% D-MEM growth medium (100 ul/well). 200 TCID50 of pseudovirus was added to each well in a volume of 50 ul and the plates were incubated for 1 hour at 37° C. TZM.b1 cells were then added ($1 \times 10^4$/well in 100 ul volume) in 10% D-MEM growth medium containing DEAE-Dextran (Sigma, St. Louis, Mo.) at a final concentration of 11 ug/ml. The final volume for each well was 250 ul. Assay controls included replicate wells of TZM.b1 cells alone (cell control), TZM.b1 cells with virus (virus control), and MuLV control. Following a 48 hour incubation at 37° C., 150 ul of assay medium was removed from each well and 100 ul of Bright-Glo luciferase reagent (Promega, Madison, Wis.) was added. The cells were allowed to lyse for 2 minutes, then 150 ul of the cell lysate was transferred to a 96-well black solid plate and luminescence was measured using a Victor 3 luminometer (Perkin Elmer, Waltham, Mass.). The 50% inhibitory concentration (IC50) titer was calculated as the immunoglobulin concentration that caused a 50% reduction in relative luminescence units (RLU) compared to the virus control wells after subtraction of cell control RLUs. M. Li et al., *J Virol* 79, 10108-10125 (2005).

ELISA. HIV-1 envelope capture ELISAs were performed as previously described with various antigens (as indicated in the text) that were directly coated (HIV-1 Ba-L SOSIP trimer, 1 ug/ml; YU2 gp120 core construct and YU2 gp120 core plus V3; 2 ug/ml) or captured (Bal-gp120 or FLSC at a concentration of 0.15 ug/m1) by antibody D7324 that had been adsorbed to the solid phase at 2 ug/ml. Y. Guan et al., *Proc Natl Acad Sci USA* 106, 3952-3957 (2009). For IEF-fractionated affinity purified IgG, 5 ng from each fraction was tested in a total assay volume of 50 ul. All IgG preparations were incubated with antigens for 1 hour at 37° C. Bound Abs were then detected with 1:1,000-diluted alkaline phosphatase (AP)-goat antihuman IgG (Southern Biotech; Birmingham, Ala.) and detected with Blue Phos Microwell Phosphatase Substrate System (KPL, Gaithersburg, Md.). All assays were performed in duplicate or repeated several times. Negative control assays were carried out with secondary antibody; background values were subtracted from all test absorbance readings.

Isolation of Plasma mAbs. Antibody species that were isolated to individual fractions were subjected to LC-MS (in addition to FFE fractions, several experiments were carried out with affinity purified fractions or cut-out IEF bands from an IEF gel). Antibody was digested with trypsin, chymotrypsin, or Glu-C overnight at 37° C. The peptides evaporated to 15 ul. The LC-MS system consisted of a Thermo Electron Orbitrap Velow ETD mass spectrometer with a Protana nanospray ion source interfaced with a Phenomenex Jupiter C18 reversed-phase capillary column. The peptide digest was fragmented with both CID and HCD. LC-MS was performed at the University of Maryland School of Pharmacy and Northwestern Proteomics Center of Excellence, none of which were involved in the data analysis. The spectra were searched with Peaks software (Bioinformatics Solutions Inc, Ontario, Calif.) against multiple B cell databases generated from the patient described below. B cell databases generated from the patient from PBMCs and Bone marrow cells with 2 different techniques from a single time point: deep sequencing and single-cell sequencing. Single-cell sequencing (Atreca, Redwood City, Calif.) was performed on memory B cells (Yu2-gp140 reactive), plasmablasts, and plasma cells ($CD38^{hi}$, CD138-).

Single Cell Sorting

All paired chain antibody sequencing was carried out on IgG cells sorted into microtiter plates at one cell per well by FACS. IgG plasmablasts were enriched from cryopreserved peripheral blood mononuclear cells (PBMCs) by gating for CD19+CD20−CD27+CD38(high)IgA-IgM-IgD-cells. Antigen-specific cells were isolated from PBMCs using fluorescently-labeled YU2 gp140 and cultured for 4 days prior to single cell sorting in IMDM medium (Invitrogen) in the presence of FBS, Pen/Strep,IL-2 (PeproTech), IL-21 (PeproTech), and rCD40 ligand (R&D Systems). Y. Li et al.,*J Virol* 80, 1414-1426 (2006). Bone marrow plasma cells were selected for high CD38 and in one experiment further sorted into CD19+CD138−, CD19+CD138+ and CD19− populations.

Paired Chain Antibody Sequencing

Generation of barcoded cDNA, PCR amplification, and 454 sequencing of IgG were performed as described in Tan et al. 2014, with the following modifications: biotinylated Oligo (dT) and RT maxima H- (Fisher Scientific Company) were used for reverse transcription, cDNA was extracted using Streptavidin C1 beads (Life Technologies), DNA concentrations were determined using qPCR (KAPA SYBR® FAST qPCR Kit for Titanium, Kapabiosystems), and amplicons were sequenced using Roche 454 Titanium sequencing.

Barcode Assignment, Sequence Assembly, Assignment of V(D)J and Identification of Mutations These steps were performed as previously described, except for the following: a minimum coverage of 10 reads was required for each heavy and light chain assembly to be acceptable. Y. C. Tan et al., Clin Immunol 151, 55-65 (2014). Wells with more than one contig for a chain were rejected from consideration unless one of the contigs included at least 90% of the reads. V(D)J assignment and mutation identification was performed using a variant of SoDA. J. M. Volpe et al., Bioinformatics 22, 438-444 (2006). Antibody amino acid sequences were aligned to heavy and light chain hidden Markov models using hmmalign. The resulting multiple sequence alignments were used to generate a neighbor-joining tree with RapidNJ. M. T. Simonsen M, Pedersen CNS, in WABI 2008, L. J. Crandall K A, Ed. (Springer, Heidelberg, 2008), vol. 5251, pp. 113-122. Mass spectrometry analysis and generation of plasma antibodies An array of whole IgG H and L amino acid sequences were translated from the database and used as a basis for interpreting the peptide data. The LC-MS derived spectra were searched against the databases independently using the following settings: Parent Mass Error Tolerance 5.0 ppm, Fragment Mass Error Tolerance 0.5 Da, Fixed modification of Carboxymethyl (58.01), False Discovery Rate for peptides 5%. Potential antibodies were ranked based on number of unique peptides in the heavy and light chain sequences. The identified VH or VL region clones were cloned into an expression vector upstream to human IgG1 constant domain sequence. Minipreps of these DNA pools, derived from suspension bacterial cultures, were used to transiently transfect 293 Freestyle cells. Transfectant supernatants containing recombinant antibodies were screened in ELISA and neutralization assays. In total, 20 mAbs were generated, and only 7 of these (mostly on the lower end of the scoring system) did not bind gp120 or neutralize HIV-1. Crystallization Initial crystal screens were done in robotic vapor-diffusion sitting drop trials using Gryphon Protein Crystallization Robot (Art Robbins Instruments) and commercially available sparse matrix crystallization screens from Molecular Dimensions (Proplex and MacroSol), Emerald BioSystems (Precipitant Wizard Screen) and Emerald BioSystems (Synergy Screen). The screens were monitored periodically for protein crystals. Conditions that produced micro crystals were then reproduced and optimized using the hanging-drop, vapor diffusion method with drops of 0.5·mu·l protein and 0.5·mu·l precipitant solution containing 0.1 M Magnesium acetate hexahydrate, 0.065M NaCl and 0.1 M MOPS pH 7.5 and incubated at 22.degree. C. The complex crystals were frozen after briefly soaking in mother liquor supplemented with 20% MPD prior to being frozen and used for data collection. Data collection and structure solution and refinement Diffraction data for N60-p23 Fab-gp120.sub.93TH057 core.sub.e complex were collected at the Stanford Synchrotron Radiation Light Source (SSRL) at the beam line BL14-1 equipped with ADSC Quantum 315 area detectors. The crystals belong to a space group P1 with the unit-cell parameters a=127.6, b=68.6, c=119.4.ANG. and .alpha.=90.degree., .beta.=111.4.degree., y=90.degree. and one N60-p23 Fab-gp120.sub.93TH057 core.sub.e complex present in the asymmetric unit (ASU). Data was processed and reduced with HKL2000. Z. Otwinowski et al., (Academic Press, 1997), vol. Volume 276, pp. 307-326. The structure was solved by molecular replacement with Phaser from the CCP4 suite based on the coordinates of gp120 (PDB:3TGT) and the VRCO1 Fab (PDB:4RFE) for the N60-p23 Fab. A. J. McCoy, Acta Crystallogr D Biol Crystallogr 63, 32-41 (2007); C. C. P. N., Acta Crystallogr D Biol Crystallogr 50, 760-763 (1994). Refinement was carried out with Refmac and/or Phenix. G. N. Murshudov et al., Acta Crystallogr D Biol Crystallogr 53, 240-255 (1997); P. D. Adams et al., Acta Crystallogr D Biol Crystallogr 58, 1948-1954 (2002). Refinement was coupled with manual refitting and rebuilding with COOT. P. Emsley et al., Acta Crystallogr D Biol Crystallogr 60, 2126-2132 (2004). The final model to a resolution of 2.4.ANG. was refined to an R-factor of 0.211 and an R.sub.free of 0.275. Data collection and refinement statistics are shown in (Table 1). Structure validation and analysis The quality of the final refined model was monitored using the program MolProbity. I. W. Davis et al., Nucleic Acids Res 32, W615-619 (2004). Structural alignments were performed using the Dali server and the program 1sqkab from CCP4 suite. The PISA webserver was used to determine contact surfaces and interface residues. E. Krissinel et al., J Mol Biol 372, 774-797 (2007). All illustrations were prepared with the PyMol Molecular Graphic suite (DeLano Scientific, San Carlos, Calif., USA).

Example 2—Identification of Antibodies from Plasma Against HIV p24

Using the same method of antibody isolation and sequencing for gp120 (Example 1), we have isolated antibodies to another part of HIV, p24. HIV-1 p24 is part of the core of HIV (Gag), and antigenically distinct from HIV-1 gp120 (Env). In addition, studies have shown that the regulation of anti-p24 antibodies is entirely different than anti-gp120 antibodies in HIV-infected patients (Binley et al., J Virol. 1997 April;71(4):2799-809). Thus, the ability to obtain these antibodies served as another control for and validation of this technique.

Patient plasma was purified as before with Protein A/G column. HIV-1 IIIB p24 recombinant protein was conjugated to agarose beads, and patient antibody run over the column and anti-p24 antibody eluted. Because we were not expecting a complex mixture of antibodies (p24 is relatively conserved and so the response against it should be simpler, compared to gp120, which as significant antigenic variation and a complex response), we used bulk digestion of the polyclonal antibody with trypsin without further fractionation. The generated peptides were run through the LC-MS and analyzed as before. Using this method we were able to generate 3 anti-HIV p24 antibodies (N60P53, N60P54, and B60P55). These antibodies reacted with p24 on 3 separate assays. The mAbs reacted with p24 Elisa (FIG. 12), HIV-1 biacore (FIG. 13), as well as HIV-1 Western blot (FIG. 14), demonstrating that this technique can be used to isolate antibodies generated against diverse epitopes. The heavy and light chain sequences are shown in FIG. 15. The mAbs N6053 and N60P54 are related using the IGHV4-31/IGHD7-27/IGHJ4 heavy chain with 96% homology and the IGKV1D-39/IGKJ1 light chain (with 94% homology), and arise from the same ancestral clone, while the mAb N60P55 arises from IGHV4-59B/IGHD3-16/IGHJ3 and IGKV3-20/IGKJ1 (FIG. 15).

What is claimed is:

1. A method of making an antibody by identifying a circulating antibody with activity from a subject comprising:
   i) subjecting biological fluid selected from the group consisting of blood, plasma and serum and combinations thereof from the subject to one or more rounds of affinity chromatography to purify the circulating antibody;
   ii) optionally further subjecting the circulating antibody to isoelectric focusing to purify the circulating antibody based on charge;
   iii) testing the purified circulating antibody for activity;
   iv) digesting the purified circulating antibody from parts i) or ii) to create an antibody fragment;
   v) subjecting the antibody fragment to mass spectrometry to generate a mass assignment and a deduced amino acid sequence of the antibody fragment;
   vi) comparing the deduced amino acid sequence with an amino acid sequence of an antibody generated from the subject's B-cells to identify an antibody sequence that matches the deduced amino acid sequence;
   vii) generating an antibody comprising light chain and heavy chain CDR sequences of the B-cell antibody that matches the deduced amino acid sequence of part vi); and
   viii) testing the antibody of part vii) for activity;
   wherein the circulating antibody with activity binds an HIV antigen selected from the group consisting of gp120, p24, gp41, p31, p17, p55, RT, rev, nef, vpu, and tat; and
   wherein the B-cells comprise bone marrow cells exhibiting a long or short-lived phenotype, wherein the B-cells have a phenotype that is CD38hi, CD19+ or CD19−, and CD138+ or CD138−.

2. The method of claim 1, wherein the circulating antibody with activity binds free gp120.

3. The method of claim 1, wherein the circulating antibody with activity is an IgG antibody.

4. The method of claim 3, wherein the circulating antibody with activity is an IgG1 antibody.

5. The method of claim 1, wherein the circulating antibody with activity has a kappa light chain.

6. The method of claim 1, wherein the circulating antibody has a lambda light chain.

7. The method of claim 1, wherein the B-cells are from blood, lymph node and bone marrow.

8. The method of claim 7, wherein the B-cells comprise plasmablasts, plasma cells, and memory B cells.

9. The method of claim 1, wherein the B-cells are analyzed by single cell PCR and/or deep sequencing to generate heavy chain and light chain amino acid antibody sequences.

10. The method of claim 1, wherein the B-cells comprise bone marrow cells having the phenotype IgA−, IgM−, IgD−, CD19+(or CD19−), CD20−, CD27+, CD38hi and CD138− (or CD138+).

11. The method of claim 1, wherein the circulating antibody binds a gp120 epitope selected from the group consisting of a CD4 binding site, a CD4 induced epitope, and a V3 epitope.

12. The method of claim 1, wherein the subject exhibits a neutralizing polyclonal antibody response that comprises circulating antibodies against gp120 epitopes comprising a CD4 binding site, a CD4 induced epitope, and a V3 epitope.

13. The method of claim 1, wherein the circulating antibody comprises less than 1% of the circulating IgG in the subject.

14. The method of claim 1, wherein the affinity chromatography comprises purifying circulating plasma IgG antibody using protein A.

15. The method of claim 1, wherein the affinity chromatography comprises purifying circulating antibody using an antigen.

16. The method of claim 1, wherein the affinity chromatography comprises purifying circulating IgG1 kappa chain antibodies.

17. The method of claim 1, wherein the affinity chromatography comprises purifying circulating IgG1 lambda chain antibodies.

18. The method of claim 1, wherein the purified circulating antibody of parts i) and/or ii) is tested in a binding and/or functional assay prior to subjecting the antibody fragments to mass spectrometry.

19. A method of identifying a circulating antibody with activity from a subject comprising
  i) subjecting biological fluid selected from the group consisting of blood, plasma and serum and combinations thereof from the subject to one or more rounds of affinity chromatography to purify the circulating antibody;
  ii) optionally further subjecting the circulating antibody to isoelectric focusing to purify the circulating antibody based on charge;
  iii) testing the purified circulating antibody for activity;
  iv) digesting the purified circulating antibody from parts i) or ii) to create an antibody fragment;
  v) subjecting the antibody fragment to mass spectrometry to generate a mass assignment and a deduced amino acid sequence of the antibody fragment; and
  vi) comparing the deduced amino acid sequence with an amino acid sequence of an antibody generated from the subject's B-cells to identify an antibody sequence that matches the deduced amino acid sequence;
    wherein the circulating antibody with activity binds an HIV antigen selected from the group consisting of gp120, p24, gp41, p31, p17, p55, RT, rev, nef, vpu, and tat; and
    wherein the B-cells comprise bone marrow cells exhibiting a long or short-lived phenotype, wherein the B-cells have a phenotype that is CD38hi, CD19+ or CD19−, and CD138+ or CD138−.

20. The method of claim 19, wherein the circulating antibody with activity binds free gp120.

21. The method of claim 19, wherein the B-cells are analyzed by single cell PCR and/or deep sequencing to generate heavy chain and light chain amino acid antibody sequences.

22. The method of claim 19, wherein the B-cells comprise circulating plasmablasts having the phenotype IgA−, IgM−, IgD−, CD19+, CD20−, CD27+, and CD38hi.

23. The method of claim 19, wherein the B-cells comprise bone marrow cells having the phenotype IgA-, IgM-, IgD-, CD19+ or CD19−, CD20−, CD27+, CD38hi and CD138+ or CD138−.

24. The method of claim 19, wherein the circulating antibody binds a gp120 epitope selected from the group consisting of a CD4 binding site, a CD4 induced epitope, and a V3 epitope.

25. The method of claim 19, wherein the subject exhibits a neutralizing polyclonal antibody response that comprises circulating antibodies against gp120 epitopes comprising a CD4 binding site, a CD4 induced epitope, and a V3 epitope.

26. The method of claim 19, wherein the affinity chromatography comprises purifying circulating IgG antibody using protein A.

27. The method of claim 19, wherein the affinity chromatography comprises purifying circulating antibody using an antigen.

28. The method of claim 19, wherein the affinity chromatography comprises purifying circulating IgG1 kappa chain antibodies.

29. The method of claim 19, wherein the affinity chromatography comprises purifying circulating IgG1 lambda chain antibodies.

30. The method of claim 19, wherein the purified circulating antibody of parts i) and/or ii) is tested in a binding and/or functional assay prior to subjecting the antibody fragments to mass spectrometry.

* * * * *